US012636271B2

(12) United States Patent
Parasassi et al.

(10) Patent No.: US 12,636,271 B2

(45) **Date of Patent: *May 26, 2026**

(54) COMBINATION COMPRISING N-ACETYL-L-CYSTEINE AND ITS USE

(71) Applicant: IASOMAI AB, Lidingö (SE)

(72) Inventors: Tiziana Parasassi, Rome (IT); Graziella Costa, Ciampino (IT); Ewa Krasnowska, Rome (IT); Eugenia Pittaluga, Rome (IT); Thomas Lundeberg, Lidingö (SE)

(73) Assignee: IASOMAI AB, Lidingö (SE)

(*) Notice: Subject to any disclaimer, the term of this patent is extended or adjusted under 35 U.S.C. 154(b) by 743 days.

This patent is subject to a terminal disclaimer.

(21) Appl. No.: 17/940,958

(22) Filed: Sep. 8, 2022

(65) Prior Publication Data

US 2023/0226009 A1 Jul. 20, 2023

Related U.S. Application Data

(60) Continuation-in-part of application No. 17/560,902, filed on Dec. 23, 2021, which is a continuation of application No. 16/401,621, filed on May 2, 2019, now Pat. No. 11,207,287, which is a continuation of application No. 15/791,290, filed on Oct. 23, 2017, now Pat. No. 10,300,038, which is a division of application No. 14/042,282, filed on Sep. 30, 2013, now Pat. No. 9,795,582, which is a continuation of application No. PCT/EP2012/054360, filed on Mar. 13, 2012.

(60) Provisional application No. 61/508,262, filed on Jul. 15, 2011, provisional application No. 61/471,162, filed on Apr. 3, 2011.

(30) Foreign Application Priority Data

Apr. 1, 2011 (SE) .................................... 1100238-3
Jul. 15, 2011 (SE) .................................... 1150696-1

(51) Int. Cl.

| | |
|---|---|
| ***A61K 31/28*** | (2006.01) |
| ***A61K 8/23*** | (2006.01) |
| ***A61K 8/44*** | (2006.01) |
| ***A61K 8/49*** | (2006.01) |
| ***A61K 8/58*** | (2006.01) |
| ***A61K 8/63*** | (2006.01) |
| ***A61K 31/198*** | (2006.01) |
| ***A61K 31/4045*** | (2006.01) |
| ***A61K 31/573*** | (2006.01) |
| ***A61K 45/06*** | (2006.01) |
| ***A61L 29/08*** | (2006.01) |
| ***A61Q 19/08*** | (2006.01) |

(52) U.S. Cl.

CPC ................ *A61K 31/28* (2013.01); *A61K 8/23* (2013.01); *A61K 8/447* (2013.01); *A61K 8/4913* (2013.01); *A61K 8/58* (2013.01); *A61K 8/63* (2013.01); *A61K 31/198* (2013.01); *A61K 31/4045* (2013.01); *A61K 31/573* (2013.01); *A61K 45/06* (2013.01); *A61L 29/08* (2013.01); *A61Q 19/08* (2013.01); *Y02A 50/30* (2018.01)

(58) Field of Classification Search

None

See application file for complete search history.

(56) References Cited

U.S. PATENT DOCUMENTS

| | | | |
|---|---|---|---|
| 4,746,674 | A | 5/1988 | Pierpaoli et al. |
| 5,330,757 | A | 7/1994 | Burke |
| 5,667,791 | A | 9/1997 | Hersh et al. |
| 5,804,594 | A | 9/1998 | Murad |
| 6,207,190 | B1 | 3/2001 | Richardson et al. |
| 8,637,573 | B2 | 1/2014 | Parasassi et al. |
| 9,585,854 | B2 | 3/2017 | Lundeberg |
| 2003/0229141 | A1 | 12/2003 | Yu et al. |
| 2004/0001817 | A1 | 1/2004 | Giampapa |
| 2004/0045566 | A1 | 3/2004 | Pera |
| 2005/0164911 | A1 | 7/2005 | Cavalieri et al. |
| 2007/0231312 | A1 | 10/2007 | Muench et al. |
| 2010/0015200 | A1 | 1/2010 | McClain et al. |
| 2011/0027771 | A1 | 2/2011 | Deng |

FOREIGN PATENT DOCUMENTS

| | | |
|---|---|---|
| CA | 2230389 | 10/1999 |
| DE | 10110418 | 9/2002 |
| EP | 0438856 | 7/1991 |
| JP | H1072339 | 3/1998 |
| JP | H11286442 | 10/1999 |

(Continued)

OTHER PUBLICATIONS

Bradlow et al. (The potential of N-Acetyl-L-Cysteine (NAC) in the treatment of Psychiatric Disorders, CNS Drugs, Mar. 22, 2022; 36(5).*

(Continued)

*Primary Examiner* — Melissa S Mercier

(74) *Attorney, Agent, or Firm* — Haynes and Boone, LLP

(57) ABSTRACT

A combination of N-acetyl-L-cysteine, selenium in the form of selenomethionine and melatonin, and a medical product or pharmaceutical composition comprising such combination, useful for the treatment of a variety of diseases and conditions is described. The combination of N-acetyl-L-cysteine, selenium in the form of selenomethionine and melatonin is also useful for cosmetic treatment of skin and as an antibacterial agent.

16 Claims, 16 Drawing Sheets

Specification includes a Sequence Listing.

(56) References Cited

FOREIGN PATENT DOCUMENTS

| | | |
|---|---|---|
| JP | 2001151153 | 6/2001 |
| JP | 2005539056 | 12/2005 |
| JP | 2009506030 | 2/2009 |
| WO | WO 1998/033494 | 8/1998 |
| WO | WO 2002/051405 | 7/2002 |
| WO | WO 2003/077900 | 9/2003 |
| WO | WO 2003/105797 | 12/2003 |
| WO | WO 2005/013951 | 2/2005 |

OTHER PUBLICATIONS

"Welcome to NCBI The National Center for Biotechnology Information advances science and health by providing access to biomedical and genomic information.", National Center for Biotechnology Information, Mar. 30, 2011, 1 page [online], [retrieved on Mar. 29, 2018]. Retrieved from the Internet: <URL:https://web.archive.org/web/20110330090453/http://www.ncbi.nlm.nih.gov>.

Akbaraly et al., "Plasma selenium and risk of dysglycemia in an elderly French population: results from the prospective Epidemiology of Vascular Ageing Study", Nutrition & Metabolism, 2010, pp. 1-7, vol. 7, No. 21, BioMed Central Ltd., London, Great Britain.

Balansky et al., "Interactions Between N-Acetylcysteine and Sodium Selenite in Modulating the Clastogenicity of Urethane and 2-Acetylaminofluorene in Mice", International Journal of Cancer, 2004, pp. 158-161, vol. 108, Wiley-Liss, Inc., Hoboken, NJ.

Bulato et al., "Effect of mercury on selenium utilization and selenoperoxidase activity in LNCaP cells", Free Radical Biology & Medicine, 2007, pp. 118-123, vol. 42, Elsevier, Amsterdam, Netherlands.

Cemeli et al., "Antioxidants and the Comet assay", Mutation Research, 2009, pp. 51-67, vol. 681, Elsevier, Amsterdam, Netherlands.

Chantret et al., "Differential expression of sucrase-isomaltase in clones isolated from early and late passages of the cell line Caco-2: evidence for glucose-dependent negative regulation", Journal of Cell Science, 1994, pp. 213-225, vol. 107, The Company of Biologists Limited, Cambridge, Great Britain.

Emonet et al., "Thiols and selenium: protective effect on human skin fibroblasts exposed to UVA radiation." (Abstract Only), PubMed, Aug. 1997, 1 page [online], [retrieved on Jan. 12, 2010]. Retrieved from the Internet: <URL: https://www.ncbi.nlm.nih.gov/pubmed/9301047?ordinalpos=3&itoll=EntrezSystem2&report=ab stract>.

García et al., "Protective role of melatonin on oxidative stress status and RNA expression in cerebral cortex and cerebellum of AbetaPP transgenic mice after chronic exposure to aluminum." (Abstract Only), Jun. 2010, PubMed, 1 page [online], [retrieved on Mar. 29, 2018]. Retrieved from the Internet: <URL: https://www.ncbi.nlm.nih.gov/pubmed/19680607?report=abstract>.

Gustafsson et al. "Global gene expression analysis in time series following N-acetyl L-cysteine induced epithelial differentiation of human normal and cancer cells in vitro" BMC Cancer, 5:75, Jul. 7, 2005, pp. 1-19.

Halder et al., "Vitiligo Update", Seminars in Cutaneous Medicine and Surgery, 2009, pp. 86-92, vol. 28, Elsevier, Amsterdam, Netherlands.

Hardeland et al., "Melatonin—A pleiotropic, orchestrating regulator molecule", Progress in Neurobiology, 2011, pp. 350-384, vol. 93, Elsevier, Amsterdam, Netherlands.

Radogna et al., "Rapid and transient stimulation of intracellular reactive oxygen species by melatonin in normal and tumor leukocytes", Toxicology and Applied Pharmacology, May 12, 2009, pp. 37-45, vol. 239, Elsevier, Amsterdam, Netherlands.

Jones, Dean P., "Radical-free biology of oxidative stress", American Journal of Physiology—Cell Physiology, Oct. 2008, pp. C849-C868, vol. 295, American Physiological Society, Bethesda, MD.

Klein, Eric A., "Selenium and Vitamin E: Interesting Biology and Dashed Hope", Journal of the National Cancer Institute, Mar. 4, 2009, pp. 283-285, vol. 101, Issue 5, Oxford University Press, Oxford, Great Britain.

Krasnowska et al. "N-acetyl-I-cysteine fosters inactivation and transfer to endolysosomes of c-Src" Free Radical Biology & Medicine, vol. 45, No. 11, Sep. 23, 2008, pp. 1566-1572 (7 total).

Lippman et al., "Effect of Selenium and Vitamin E on Risk of Prostate Cancer and Other Cancers The Selenium and Vitamin E Cancer Prevention Trial (SELECT)", Journal of American Medical Association, Jan. 7, 2009, pp. 39-51, vol. 301, No. 1, American Medical Association, Chicago, IL.

Livak et al., "Analysis of Relative Gene Expression Data Using Real-Time Quantitative PCR and the 2(-Delta Delta C(T)) Method", Methods, 2001, pp. 402-408, vol. 25, Elsevier Science (USA), New York, NY.

Look et al., "Sodium selenite and N-acetylcysteine in antiretroviral-naive HIV-1-infected patients: a randomized, controlled pilot study." (Abstract Only), May 1998, 1 page [online], [retrieved on Jan. 12, 2010]. Retrieved from the Internet: <URL: https://www.ncbi.nlm.nih.gov/pubmed/9650013?ordinalpos=2&itool=EntrezSystem2&report=abstract>.

Nickel et al., "Tobramycin Resistance of Pseudomonas aeruginosa Cells Growing as a Biofilm on Urinary Catheter Material", Antimicrobial Agents and Chemotherapy, Apr. 1985, pp. 619-624, vol. 27, No. 4, American Society for Microbiology, Washington, DC.

Parasassi et al. "Differentiation of normal and cancer cells induced by sulfhydryl reduction: biochemical and molecular mechanisms" Cell Death and Differentiation, vol. 12, No. 10, May 27, 2005, pp. 1285-1296 (12 total).

Parasassi et al., "Thiol Redox Transitions in Cell Signaling: a Lesson from N-Acetylcysteine", The Scientific World Journal, 2010, pp. 1192-1202, vol. 10, TheScientificWorld, Cairo, Egypt.

Patent Office Of The Russian Federation, Office Action, Jan. 25, 2016, 5 pages, Russian Application No. 2013146213/15, filed Jul. 17, 2000.

PCT International Search Report, PCT Patent Application No. PCT/EP2012/054360, Jul. 3, 2012, 7 pages.

Pendyala et al. "Pharmacokinetic and Pharmacodynamic Studies of N-Acetylcysteine, a Potential Chemopreventive Agent during a Phase I Trial" Cancer Epidemiology, Biomarkers & Prevention, vol. 4, No. 3, Apr./May 1995, pp. 245-251 (7 total).

Safarinejad et al., "Efficacy of selenium and/or N-acetyl-cysteine for improving semen parameters in infertile men: a double-blind, placebo controlled, randomized study." (Abstract Only), 2009, 1 page [online], [retrieved on Jan. 12, 2010]. Retrieved from the Internet: <URL: https://www.ncbi.nlm.nih.gov/pubmed/19091331?ordinalpos=1&itool=EntrezSystem2&report=abstract>.

Sardar et al., "Antioxidant associated chemoprevention by selenomethionine in murine tumor model", Molecular and Cellular Biochemistry, 2000, pp. 17-25, vol. 206, Netherlands.

Sener et al., "Melatonin and N-acetylcysteine have beneficial effects during hepatic ischemia and reperfusion", Life Sciences, 2003, pp. 2707-2718, vol. 72, Elsevier, Amsterdam, Netherlands.

Setaro et al., "Irregularity skin index (ISI): a tool to evaluate skin surface texture", Skin Research and Technology, 2001, pp. 159-163, vol. 7, Munksgaard, Copenhagen, Denmark.

Wölfler et al., "Prooxidant activity of melatonin promotes fas-induced cell death in human leukemic Jurkat cells", Federation of European Biochemical Societies, 2001, pp. 127-131, vol. 502, Elsevier, Amsterdam, Netherlands.

Yalçin et al., "Synergistic action of sodium selenite and N-acetylcysteine in acetaminophen-induced liver damage." (Abstract Only), May 2008, 1 page [online], [retrieved on Jan. 12, 2010]. Retrieved from the Internet: <URL: https://www.ncbi.nlm.nih.gov/pubmed/18715889?ordinalpos=2&itool=EntrezSystem2&report=abstract>.

* cited by examiner

COMBINATION COMPRISING N-ACETYL-L-CYSTEINE AND ITS USE

CROSS-REFERENCE TO RELATED APPLICATIONS

This application is a continuation-in-part application of U.S. patent application Ser. No. 17/560,902 filed on Dec. 23, 2021, which is a continuation of U.S. patent application Ser. No. 16/401,621 filed May 2, 2019 (now U.S. Pat. No. 11,207,287 issued Dec. 28, 2021), which is a continuation of U.S. patent application Ser. No. 15/791,290 filed on Oct. 23, 2017 (now U.S. Pat. No. 10,300,038 issued May 28, 2019), which is a divisional of U.S. patent application Ser. No. 14/042,282 filed on Sep. 30, 2013 (now U.S. Pat. No. 9,795,582 issued Oct. 24, 2017), which is a continuation of International Patent Application No. PCT/EP2012/054360 filed on Mar. 13, 2012, which claims priority to and the benefit of Swedish Patent Application No. 1100238-3 filed on Apr. 1, 2011, U.S. Provisional Patent Application No. 61/471,162 filed on Apr. 3, 2011, Swedish Patent Application No. 1150696-1 filed on Jul. 15, 2011, and U.S. Provisional Patent Application No. 61/508,262 filed on Jul. 15, 2011, the contents of each of which is hereby incorporated herein in its entirety by express reference thereto.

REFERENCE TO AN ELECTRONIC SEQUENCE LISTING

The contents of the electronic sequence listing (SEQUENCE LISTING.xml; Size: 17 kB; and Date of Creation: Sep. 8, 2022) is herein incorporated by reference in its entirety.

TECHNICAL FIELD

The present invention relates to a combination of N-acetyl-L-cysteine, selenium, such as selenomethionine, and melatonin, and to a pharmaceutical composition comprising such combination, useful for the treatment of a variety of diseases and conditions, e.g., benign and malignant neoplasia including various types of cancers, autoimmune diseases, neurodegenerative diseases, endocrinological diseases, type 2 diabetes, all types of fibrosis, amyloidosis, endometriosis, polycystic ovary syndrome, dysmenorrhea, dermatological diseases including vitiligo, alopecia and psoriasis, and anxiety disorders including sleep disorder and fatigue. The combination is also useful as an antibacterial agent and for cosmetic purposes.

BACKGROUND

Control and modulation of intracellular reduction and oxidation (redox) environment is of fundamental relevance for cellular processes. For example, loss in the redox control of the cell cycle can lead to a more oxidant environment, promoting the progression from G1 to S phase and therefore leading to aberrant proliferation, a hallmark of various neoplasies. Also, most chronic inflammatory diseases are accompanied by a loss of redox control. Dysregulation towards a more oxidized intracellular environment is thus associated with aberrant proliferation and inflammation and is therefore ultimately related to diseases such as, but not limited to, cancer, neurodegenerative disease, diabetes, aberrant wound healing, and fibrosis. In addition, in oxidative environments, proteins can be oxidative modified, a process often followed by the formation of aggregates, also in the form of amyloids.

The functional status of cells is under the control of external stimuli, affecting the function of critical proteins and gene expression. Signal sensing and transduction by messengers to specific effectors operate by post-translational modification of proteins, among which thiol (—SH) reduction/oxidation (redox) switches play a fundamental role. Sensitive cysteine residues in proteins constitute the mentioned redox switches, where "sensitive" indicates a lower electrochemical potential of the cysteine/cystine redox couple (SH/S—S) resulting from a specific protein conformation. Thiol redox switches in for example enzymes, receptors, transporters, transcription factors, structural elements, regulators of protein trafficking synthesis and degradation, and the cytoskeletal structure all deeply affect the overall cellular homeostasis.

The production of oxidants in mammalian cells derives from fundamental processes such as glycolysis and mitochondrial respiratory chain, ending up with the production of reactive oxygen species, among them the most stable is represented by hydrogen peroxide ($H_2O_2$). The produced oxidants must be under a strict control and a reversal of the oxidative pathway is necessary. The redox control is affected by several low molecular weight substances and a complex network of enzymes, including among others, glutathione reductase (GR) and the family of selenium-dependent glutathione peroxidases (GPx). Reduced glutathione (GSH) is a dominant low molecular weight thiol species in most organisms, whose redox potential is used by the many enzymes in charge of the redox control in cells, including GR and GPx, to recycle their own redox status.

Reduced glutathione (GSH) is a tripeptide present in all human tissues at relatively high concentrations, even above 10 mM. It has many important functions in the body. As described above, it can be regarded as the major endogenous antioxidant, participating: 1) in the control of the cell redox status; and 2) in the control of the oxidation status of proteins relevant in signaling, including the receptors of external stimuli (e.g. hormone receptors). It plays a fundamental role in numerous metabolic and biochemical reactions such as DNA synthesis and repair, protein synthesis, prostaglandin synthesis, amino acid transport, and enzyme activation. It also participates in the regulation of the nitric oxide cycle, detoxifies many carcinogens and other xenobiotics and has an essential role for optimal response in many parts of the immune system. Thus, most systems in the body can be affected by the state of the glutathione system. For instance, states of glutathione deficiency include HIV/AIDS, chemical and infectious hepatitis, prostate and other cancers, cataracts, Alzheimer's disease, Parkinson's disease, chronic obstructive pulmonary disease, asthma, radiation poisoning, malnutritive states, arduous physical stress and aging, and has been associated with suboptimal immune response. Low glutathione is also strongly implicated in wasting and negative nitrogen balance, as seen in cancer, AIDS, sepsis, trauma, burns and even athletic overtraining, as well as in bipolar disorder, major depressive disorder, and schizophrenia.

Glutathione is synthesized from the amino acids L-cysteine, L-glutamic acid and glycine. The sulfhydryl (thiol) group (SH) of the cysteine serves as a proton donor and is responsible for the biological activity of glutathione. The supply of cysteine is the rate-limiting factor in glutathione synthesis by the cells, since cysteine is a relatively rare nutrient. Glutathione supplementation has thus been suggested for various diseases and symptoms.

However, glutathione taken orally can be degraded already in the stomach and is not well absorbed across the gastrointestinal tract. Thus raising glutathione levels through direct supplementation of glutathione is difficult. Instead supplements of agents that serve as glutathione precursors are used to increase the plasma concentration of glutathione. N-acetyl-L-cysteine (NAC in the following) is a simpler molecule than glutathione, diffuses freely in almost all tissues and cells and is the most bioavailable precursor of glutathione. Among the several thiol agents tested for their efficacy in modulating cellular redox status, NAC holds most promise for human use. A relevant advantage in the clinical use of NAC is the virtual absence of side effects. This compound has been long available for the clinic as a mucolytic agent and as an antidote after paracetamol poisoning.

In recent years NAC has also been acknowledged as having other beneficial properties. For example, NAC has been reported to have an anti-inflammatory effect and has been added to the family of non-steroidal anti-inflammatory drugs (NSAIDs). The inventors of the present disclosure have previously shown that in mammalian cells, in vitro, NAC inhibits proliferation and promotes quiescence, further evolving in terminal differentiation (WO 02/051405 A1, T. Parasassi, et. al. (Cell Death and Differentiation (2005), Vol. 12, No. 10, pages 1285-1296); E. K. Krasnowska et. al. (Free Radicals Biology and Medicine 2008, 45(11):1566-72) and A. C. Gustafsson et. al. (BMC Cancer (2005), 5:75). NAC has in this context been found to possess a marked antiproliferative effect on cancer cells and has also been found to be effective in the treatment of endometriosis. Additionally it has been used in the treatment of polycystic ovary syndrome (PCOS) as well as for treatment of various other diseases and conditions, e.g. as a nephroprotective agent, interstitial lung disease, schizophrenia, bipolar disorder and depression, and has been suggested for various other uses.

Thus, NAC is effective for many uses. Nevertheless, prolonged NAC treatments result in a decreased plasma level of NAC, so that its effective concentration must be increased and the risk of undesired side effects accordingly increases (L Pendyala and P J Creaven, Cancer Epidemiol Biomarkers Prev 1995; 4:245-251). In order to counteract the declining effect of NAC, pulsed treatments were proposed, to allow for a washout period. Another possible solution would be of reducing the concentration at which NAC is effective, which would be advantageous also for short term treatments.

There has been a wide recent interest in the protecting and/or therapeutic role of both selenium (Se in the following) and melatonin (Mel in the following). Se supplementation has for example been suggested for prevention of cancer, as an antioxidant or immune enhancer. Likewise, melatonin has been studied for the treatment of cancer, immune diseases and various other disorders. Despite this, controversial effects of these two substances were also reported. For instance, Mel has been acknowledged for its antioxidant action, but was sometimes also reported to act as a pro-oxidant (Cemeli E, Baumgartner A, Anderson D. Mutat Res. 2009; 681:51-67; Wölfler A, Caluba H C, Abuja P M et al. FEBS Lett. 2001; 502(3):127-31; Radogna F et al. Toxicology and Applied Pharmacology 2009; 239:37-45).

Regarding Se, a large trial showed that the expected prevention of prostate cancer or of other cancers was not achieved (Lippman S M et al., Journal of American Medical Association. 2009; 301(1):39-51). E A Klein (J Natl Cancer Inst. 2009; 101: 283-285) concluded with the cautionary lesson that "well-performed large-scale controlled trials do not always validate what we believe biology indicates and that our model systems are imperfect measures of clinical outcomes in the real world." Also, although a preventive role of Se on the risk of diabetes was reported and ascribed to its "insulin-like" activity and to the antioxidant properties of the selenoenzymes, a prospective study did not report any significant relationship between selenium and the risk of diabetes (Akbaraly T N et al., Nutr Metab (Lond). 2010; 7:21).

Balansky et al., "Interactions between N-acetylcysteine and sodium selenite in modulating the clastogenicity of urethane and 2-acetylaminofluorene in mice", Int. J. Cancer, Vol. 108, 2004, pp. 158-161, discloses the use of a combination of NAC and Se for attenuating the adverse effects of cytotoxic drugs and chemopreventive agents in the treatment of cancer.

Safarinejad et al., "Efficacy of selenium and/or N-acetylcysteine for improving semen parameters in infertile men: a double-blind, placebo controlled, randomized study", J. Urol., Vol. 181, No. 1, 2009, pp. 741-751, Epub December 2008, discloses the use of NAC and Se in combination or separately for improving semen quality in infertile men. Administering NAC and Se in combination resulted in additive beneficial effects.

Yalçin et al., "Synergistic action of sodium selenite and N-acetylcysteine in acetaminophen-induced liver damage", Hum. Exp. Toxicol., Vol. 27, No. 5, 2008, pp. 425-429, discloses the use of NAC and Se in combination or separately for treatment of acetaminophen overdosing. NAC and Se in combination were found to give better protection against hepatotoxicity compared to either agent alone.

Emonet et al., "Thiols and selenium: protective effect on human skin fibroblasts exposed to UVA radiation", J. Photochem. Photobiol., Vol. 40, No. 1, 1997, pp. 84-90, discloses the use of NAC and Se in combination to protect cells against UVA damage.

Look et al., "Sodium selenite and N-acetylcysteine in antiretroviral-naive HIV-1-infected patients: a randomized, controlled pilot study", J. Clin. Invest., Vol. 28, No. 5, 1998, pp. 389-397, discloses a combined oral administration of NAC and Se with the objective to improve blood count and reduce viral load in patients with HIV.

Sener et al., "Melatonin and N-acetylcysteine have beneficial effects during hepatic ischemia and reperfusion", Life Sciences, Vol. 72, 2003, pp. 2707-2718, discloses the use of NAC and Mel alone or in combination to treat hepatic ischemia. Mel was found more potent than NAC, and the combination of the two was found to be more effective than either alone.

WO 03/077900 A1 and US 2005/0164911 A1 disclose a method for preventing the development of cancer or neurodegenerative diseases by administering NAC, melatonin, or a combination thereof, as well as a medicament comprising NAC and Mel.

WO 00/531376 describes a composition containing cysteine, selenium and melatonin together with a number of other components. US 2007/0231312, US 2011/027771, WO 98/33494 and U.S. Pat. No. 6,207,190 all describe different formulations containing among other things, NAC, Se and Mel. Further, US 2004/045566 describes a composition containing glutathione, selenium and melatonin for absorbing dangerous component from tobacco smoke. None of the said documents describes the use of selenomethionine.

In all documents referred to in the prior art selenium is used as such.

SUMMARY

The present disclosure provides a solution to the problem of increasing the efficacy of NAC. In one embodiment, a medical product or pharmaceutical combination providing increased efficacy of N-acetyl-L-cysteine (NAC) is provided. In another embodiment, a medical product or pharmaceutical combination providing increased efficacy of NAC for use in the treatment of diseases in mammals, such as humans, e.g. benign and malignant iperproliferations including various types of cancers, autoimmune diseases, neurodegenerative diseases, endocrinological diseases, type 2 diabetes, all types of fibrosis, amyloidosis, endometriosis, polycystic ovary syndrome, dysmenorrhea, dermatological diseases including vitiligo, alopecia and psoriasis and bacterial infections, and anxiety disorders including sleep disorder and fatigue, is provided. In yet another embodiment, a medical product providing increased efficacy of NAC for use as an antibacterial agent and for cosmetic purposes is provided.

The present disclosure shows that the effect of N-acetyl-L-cysteine (NAC) is enhanced when NAC is administered together with selenium (Se), in the form of selenomethionine, and melatonin (Mel). Selenomethionine and Mel in combination strongly increase NAC efficacy and also allow a reduction in NAC concentration, thus ameliorating its efficacy in both short term and prolonged treatments. After testing in vitro and in vivo the efficacy of this combinatorial treatment, with NAC, Se (e.g. in the form of selenomethionine, SeMet in the following) and Mel, it was shown that undesirable effects of Se and Mel are avoided.

Thus the present disclosure provides a combination of NAC, SeMet and Mel useful for the treatment of a variety of diseases and conditions, e.g. benign and malignant iperproliferations including various types of cancers, autoimmune diseases, neurodegenerative diseases, endocrinological diseases, diabetes, all types of fibrosis, amyloidosis, endometriosis, polycystic ovary syndrome, dysmenorrhea, dermatological diseases, bacterial infections, and anxiety disorders including sleep disorder and fatigue. The combination is also useful as an antibacterial agent and for cosmetic purposes. In addition, the present disclosure provides a medical product and a pharmaceutical composition comprising said combination, as well as a method of treatment comprising simultaneous administration of NAC, SeMet and Mel to a patient.

In one aspect, the present disclosure provides a medical product comprising, separately or together, N-acetyl-L-cysteine, selenomethionine and melatonin, and/or physiologically acceptable salts thereof. By "separately" is meant that the three substances are part of the medical product, but may be provided in separate compartments, as separate units, of the medical product. By "together" is meant that the three substances may alternatively be provided in the same part of the medical device, e.g. as a mixture. The medical product is in one aspect of the disclosure used for simultaneous, sequential or separate combinatorial administration to a mammal.

In one embodiment, the components of the medical product are for oral administration; e.g. N-acetyl-L-cysteine for administration at a dose of 5-45 mg/kg/day, selenium, in the form of selenomethionine, for administration at a dose of 0.4-1.2 μg/kg/day and melatonin for administration at a dose of 0.02-0.08 mg/kg/day. The medical product is in one embodiment a pharmaceutical composition comprising N-acetyl-L-cysteine, selenium in the form of selenomethionine, and melatonin.

The medical product comprising, separately or together, N-acetyl-L-cysteine, selenium in the form of selenomethionine, and melatonin is in another embodiment for epicutaneous administration. In such medical product, N-acetyl-L-cysteine is in one embodiment for administration at a concentration of 3-10 wt-%, selenium in the form of selenomethionine, is for administration at a concentration of 0.3-1 wt-% and melatonin is for administration at a concentration of 0.01-0.2 wt-%. In one embodiment, the medical product is a pharmaceutical composition comprising N-acetyl-L-cysteine, selenium, in the form of selenomethionine, and melatonin.

In one embodiment, the medical product is for treatment of benign or malignant neoplasies, including various types of cancers. In another embodiment, it is for cosmetic treatment of skin and for treatment of dermatological diseases. The medical product may also be used for the treatment of autoimmune diseases, neurodegenerative diseases, endocrinological diseases, type 2 diabetes, all types of fibrosis, amyloidosis, endometriosis, polycystic ovary syndrome, dysmenorrhea and other diseases, and anxiety disorders including sleep disorder and fatigue. In one embodiment, the medical product is for use as an antibacterial agent.

The medical product, comprising N-acetyl-L-cysteine, selenium in the form of selenomethionine and melatonin, is in another aspect of the disclosure for use as an antibacterial agent, for use in, together with, or on the surface of a medical device that is adapted for use in contact with body fluids. The medical product may for instance be used in a coating for such a medical device, or may be incorporated into the material, e.g. plastics, of such a medical device. In one embodiment of the disclosure, N-acetyl-L-cysteine, selenium in the form of selenomethionine, and melatonin are comprised in a hydrogel coating for a medical device. The medical product for use as an antibacterial agent may further comprise additional active compounds such as germicidal drugs, noble metal solutions and/or dexamethasone.

In one aspect, the present disclosure provides an antibacterial agent comprising, separately or together, N-acetyl-L-cysteine, selenium in the form of selenomethionine, and melatonin, and/or physiologically acceptable salts thereof. The antibacterial agent is in one embodiment for use in a hydrogel coating for a medical device. In another embodiment, it is for integration with the plastics of a medical device.

In another aspect, the present disclosure provides a medical device comprising a medical product comprising N-acetyl-L-cysteine, selenium in the form of selenomethionine, and melatonin, and/or physiologically acceptable salts thereof and optionally an additional active compound such as germicidal drugs, noble metal solutions and/or dexamethasone.

In one aspect, the present disclosure provides use of a medical product comprising, separately or together, N-acetyl-L-cysteine, selenium in the form of selenomethionine and melatonin, and/or physiologically acceptable salts thereof, for the treatment of benign and malignant neoplasia including various types of cancers, autoimmune diseases, neurodegenerative diseases, endocrinological diseases, type 2 diabetes, all types of fibrosis, amyloidosis, endometriosis, polycystic ovary syndrome, dysmenorrhea, dermatological diseases including vitiligo, alopecia or psoriasis or bacterial infections, and anxiety disorders including sleep disorder and fatigue. The disclosure also provides use of the medical product for cosmetic treatment of skin and as an antibacterial agent with a medical device that is adapted for use in contact with body fluids.

In one aspect, the present disclosure provides a method of treatment of a disease, or for cosmetic purposes, comprising simultaneous, sequential or separate combinatorial administration of N-acetyl-L-cysteine, selenium in the form of selenomethionine and melatonin, and/or physiologically acceptable salts thereof, to a human or mammal patient. The disease or cosmetic purpose is selected from benign and malignant neoplasia including various types of cancers, autoimmune diseases, neurodegenerative diseases, endocrinological diseases, type 2 diabetes, all types of fibrosis, amyloidosis, endometriosis, polycystic ovary syndrome, dysmenorrhea, dermatological diseases including vitiligo, alopecia or psoriasis or bacterial infections, cosmetic treatment of skin, or anxiety disorders including sleep disorder and fatigue.

BRIEF DESCRIPTION OF THE FIGURES

Embodiment of the present invention will be explained in more detail in the following description, referring to the enclosed figures, where.

DETAILED DESCRIPTION

NAC

N-acetyl-L-cysteine (NAC) is a well-known low molecular weight pharmaceutical drug, with the chemical formula

NAC

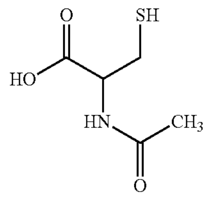

For the purpose of the present invention NAC may also be administered in its dimeric form (di-NAC).

NAC has been found to exert molecular and physiological effects through various mechanisms. The features of NAC are mainly related to its thiol group, which makes it effective in most biochemical pathways were the glutathione (GSH) acts. NAC is processed by cells to L-cysteine and is used in the de novo synthesis of GSH, thus being considered a precursor of GSH.

Figure 1:
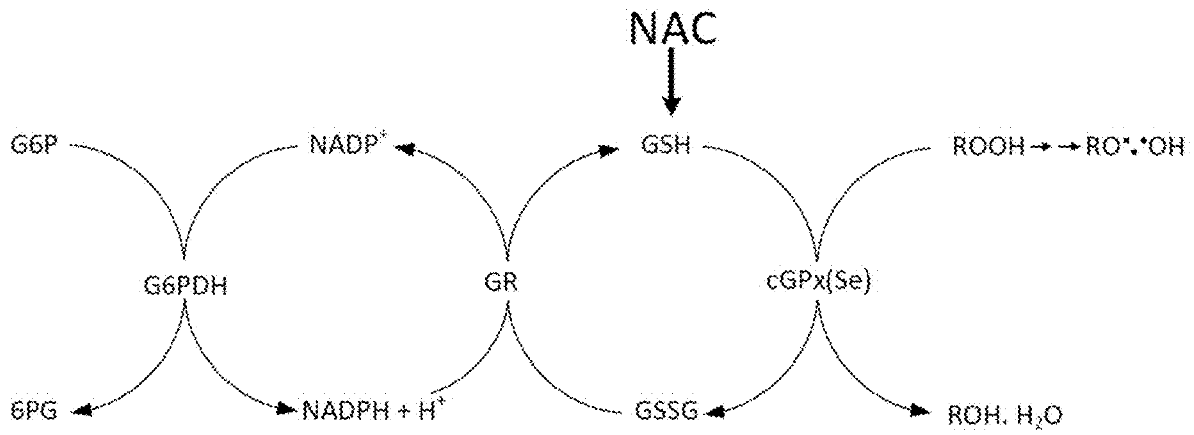
FIG. 1 shows the metabolic recycling of glutathione (GSH) by selenium-dependent glutathione peroxidase (cGPx(Se)) and glutathione reductase (GR). The activity of GR requires NADPH which is supplied by the activity of the enzyme glucose-6-phosphate dehydrogenase (G6PDH). G6P: glucose-6-phosphate; 6PG: 6-phosphogluconate; RO·: alkoxyl radical; ·OH: hydroxyl radical; ROOH: hydroperoxide.

Although details of NAC mechanisms of action are not completely understood, undoubtedly they have to be attributed to its thiol group. It is thus involved in the complex redox cycling of thiol groups in the cell, and thereby affects the regulation of the redox state of the cell as well as intracellular and intercellular signaling. In this redox cycling several enzymes act whose redox transitions occur via the oxidation/reduction of glutathione (GSH). There is previous evidence of NAC involvement in this picture, as summarized in FIG. 1, NAC having a similar or even higher efficiency as compared to GSH. In this respect, NAC can be considered a potent antioxidant.

Of extreme physiological importance is the disulfide formation and breakage cycle, a common mechanism by which protein activity and cellular signaling is regulated. Enzymes such as protein tyrosine phosphatases and tyrosine kinases, for example, play pivotal roles in the control of the cell cycle, cell proliferation and differentiation, and many of them are regulated by the redox state of their cysteines.

NAC has been and still is largely used as a mucolytic agent, where the mode of action is generally attributed to the redox breakage of sensitive cysteine disulfur bridges in the mucus proteins. In addition NAC has been the prime treatment of paracetamol poisoning.

In recent years, NAC has also been acknowledged as having other beneficial properties. NAC has for instance been reported to have an anti-inflammatory effect, a reason for its addition to the family of non-steroidal anti-inflammatory drugs (NSAIDs). NAC has further been found to inhibit cell proliferation and promote quiescence, further evolving in terminal differentiation. NAC has in this context been found to possess a marked antiproliferative effect on cancer cells and has also been found to be effective in the treatment of endometriosis. For example, the present inventors relatively recently found that NAC possesses a marked antiproliferative effect on cancer cells of epithelial origin (Cell Death and Differentiation 2005, 12(10): 1285-1296; BMC Cancer 2005, 5: 75).

The antiproliferative effect of NAC, in the study of cancer, was not related to cell death or to toxicity but, instead, was due to the activation of a physiological differentiation pathway, which can be regarded as a normalization of cell functions towards the tissue of origin.

A relevant advantage in the use of NAC is the virtual absence of side effects. A disadvantage is its decreased efficacy in prolonged treatments, with a reported decline in plasma levels so that the required dose increases, thereby also increasing the risk of some undesired effects.

NAC in Combination with Se and Mel

On this basis, the present inventors aimed at a reduction in the effective NAC dose by the contemporary use of other drugs that can exert a synergism with NAC. A reduction in NAC effective dose is useful in both long-term and short-term treatments. For that purpose the attention was focused to the enzyme network governing thiol redox cycling, particularly those reactions involving glutathione recycling by means of enzymes such as glutathione peroxidase (GPx) and glutathione reductase (GR). The focus on the flow of these redox reactions is justified by the observation that they account for nearly 99.9% of redox reactions in biology (DP Jones. Am. J. Physiol. Cell Physiol. 2008; 295:C849-C868) and that NAC action should be mostly related to a modification of the activity of these multiple enzymes (Parasassi T, Brunelli R, Costa G, et al. TheScientificWorldJOURNAL 2010; 10:1192-1202).

A decrease in the expression of GR after prolonged treatments with NAC has been reported (L Pendyala and P J Creaven, Cancer Epidemiol Biomarkers Prev 1995; 4:245-251). Reports also exist showing that Mel supplementation may yield an increased expression and/or activity of GR and also of another relevant enzyme in thiol redox reaction: the glutathione peroxidase (GPx) (Hardeland R, Cardinali D P, Srinivasan V, et al. Prog Neurobiol. 2011; 93(3):350-84, Epub Dec. 28, 2010; Garcia T, Esparza J L, Giralt M, et al., Biol Trace Elem Res. 2010; 135:220-32).

In this picture, Se represents a cofactor of several glutathione peroxidases (GPx). Se is necessary GPx activity (see for instance Bulato et al. Free Radic Biol Med. 2007; 42:118-23), and does not exert any specific antioxidant action in the absence of the GPx enzymes.

The present inventors therefore reasoned that to ensure a balanced action, devoid of undesired effects, Se had to be in the form of SeMet and administered together with Mel, i.e. in conditions where GR and GPx are stimulated and GPx can fully exert its activity. In this context, NAC could warrant the reduction potential for the overall kinetics to proceed—in this, eventually being more effective than glutathione (GSH).

On the basis of the biochemistry of the thiol redox system, the present inventors aimed at increasing the effect of NAC, at reducing the therapeutic concentration of NAC and to assure NAC efficacy in prolonged treatments. The purpose was achieved by stimulation of elements present in the thiol redox system.

With the aim of: 1) restoring/enhancing the expression/activity of enzymes in charge of the thiol signaling redox control; 2) reestablishing the proper NAC action even in prolonged treatments; and 3) reducing the effective NAC concentration, NAC treatment was combined with selenium in the form of selenomethionine and melatonin supplementation. This combination was inspired by the requirement of selenium for the activity of GPx, and by the reported effect of melatonin in increasing the expression/activity of GR and possibly of GPx.

Thus, the present disclosure is based on the purpose of enhancing NAC action through enhancement of the thiol redox system by:

1) stimulating the activity of glutathione peroxidase (GPx) by Se supplementation, in the form of selenomethionine (SeMet), which is a bioavailable form of Se.
2) The use of selenomethionine instead of selenium is very important for the effect. [2) increasing the expression and/or activity of glutathione reductase (GR) and glutathione peroxidase (GPx) by Mel.

NAC action in combination with these two additional substances was verified by testing the antioxidant, antiproliferative and differentiating effects of NAC. The combinatorial effect and possible synergy between NAC, Mel and Se in the form of SeMet was tested in vitro by using two cell lines challenged with an oxidative stimulus (Examples 3 and 4), as well as in vivo in a patient with vitiligo and in a dermatological study (Examples 1 and 2).

With regard to the antioxidant effect of NAC in the thiol redox system, measured as a decrease in the stimulated production of hydrogen peroxide, it was found that:

1) NAC action is definitely enhanced by this association. In several cases NAC was almost three times more effective in combination with SeMet and Mel than by itself.
2) NAC concentration could be decreased, a similar effect being reached using less than half of the concentration.
3) Surprisingly, in some cellular systems, an unfavorable oxidant effect was observed when combining only two of the substances, i.e. NAC+SeMet or of NAC+Mel.

This is surprising since these combinations are reported as beneficial in the scientific literature (Safarinejad M R. J Urol. 2009; 181:741-51. Yalcin S et al. Hum Exp Toxicol. 2008; 27:425-9). In contrast, it was observed that the combination of the three substances restored a cell protection, with a final effect of an almost complete absence of oxidative effect.

With regard to the effect of NAC relating to decreasing cell proliferation and inducing a differentiation process, it was found that:

1) the antiproliferative action of NAC is doubled by the combination with SeMet and Mel as compared to use of NAC by itself.
2) the differentiating action of NAC was definitely enhanced by the above combination, being 30-50% higher as compared to use of NAC by itself, depending on the specific marker.
3) by analyzing some specific differentiation markers, it was observed that the combinations of NAC+SeMet or NAC+Mel had an effect comparable to the combination of the three substances. Nevertheless, there is a clear trend to an overall increased NAC action when the three substances are used in combination.

Administration

The novel combination described herein, of NAC, Se, in the form of SeMet and Mel, may be administered to a mammal, such as a human, simultaneously, sequentially or separately in combination. By "simultaneous combinatorial administration" is meant that all three substances are administered together to the mammal at the same point in time. By "sequential combinatorial administration" is meant that the three substances are administered to the mammal during the same period of treatment, e.g. during the same day of treatment, week(s) of treatment or month(s) of treatment, such that all substances are present in the mammal in combination, the substances being administered, i.e. given to the mammal at different time points in a set order. By "separate combinatorial administration" is meant that the three substances are likewise administered to the mammal during the same period of treatment such that all substances are present in the mammal in combination, but the substances being administered, i.e. given to the mammal at different time points in an irregular order administration may be topical or systemic (either enteral or parenteral). Typical ways of administration include oral administration and epicutaneous administration. Other possible ways of administration include intravenous, intradermal, subcutaneous, intramuscular, intravaginal, intrauterine, intraperitoneal, rectal, nasal, intrathecal, inhalational and intravesical administration.

Formulations

The combination of NAC, SeMet and Mel according to the present disclosure may be administered as separate pharmaceutical formulations/compositions, each comprising only one of the three active ingredients, i.e. NAC or SeMet or Mel respectively. Alternatively the combination may be administered in a pharmaceutical composition comprising two of or all three of the active ingredients. In either case, pharmaceutical compositions comprising either only one or combinations of NAC and/or SeMet and/or Mel may be prepared in a manner per se known by a person skilled in the pharmaceutical art.

The pharmaceutical composition may for instance be adapted for oral administration. Such compositions could be administered in different forms, such as tablets. Other forms, such as capsules, suppositories, solutions, suspensions, syrups or the like are also conceivable. In pharmaceutical formulations in the form of dosage units for oral administration, the active ingredient or ingredients may be mixed with a solid, powdered carrier or excipient that serves as a vehicle or medium for the active ingredient, such as lactose, saccharose, sorbitol, mannitol, starch, amylopectin, cellulose derivatives, gelatin, citric acid, sodium citrate, sodium (acid) carbonate or another suitable carrier; stabilizing substances such as alkaline compounds e.g. carbonates, hydroxides and oxides of sodium, potassium, calcium, magnesium and the like as well as with lubricating agents such as magnesium stearate, calcium stearate, sodium stearyl fumarate and polyethylene glycol waxes. The mixture is then processed into granules or pressed into tablets. Granules and tablets may be coated with an enteric coating which protects the active compound from acid catalyzed degradation as long as the dosage form remains in the stomach. The enteric coating is chosen among pharmaceutically acceptable enteric coating materials e.g. beeswax, shellac or anionic film-forming polymers and the like, and in some embodiments, in combination with a suitable plasticizer. To the coating, various dyes may be added in order to distinguish among tablets or granules with different amounts of the active compound present.

Soft gelatin capsules may be prepared with capsules containing a mixture of the active compound, vegetable oil, fat or other suitable vehicle for soft gelatin capsules. Soft gelatin capsules may also be enteric coated as described above.

Hard gelatin capsules may contain granules or enteric coated granules of the active compound. Hard gelatin capsules may also contain the active compound in combination with a solid powdered carrier such as lactose, saccharose, sorbitol, mannitol, potato starch, amylopectin, cellulose derivatives or gelatin. The capsules may be enteric coated as described above.

One option is to provide NAC and/or SeMet and/or Mel in a slow-release formulation (also denoted sustained-release or controlled-release). By being able to reduce the rate of diffusion and uptake of active substances into the blood stream such a formulation enables administration of a larger dose at longer intervals. The dose is then distributed in the blood over a long time in small quantities, e.g. over 12+12 hours in the case of a twice-a-day regimen scheme. Many different technologies and formulations for slow-release are since long known in the art and may be applied with the present disclosure. In such technologies the active substance is for example encapsulated in a coating or matrix that is insoluble or less soluble in the body fluid where it is administered. Formulations having a combined effect of slow-release and gastric protection is also possible and may be used within the present disclosure.

Liquid preparation for oral administration may be prepared in the form of syrups or suspensions, e.g. solutions or suspensions containing from 0.2% to 20% by weight of the active ingredients and the remainder consisting of sugar or sugar alcohols and a mixture of ethanol, water, glycerol, propylene glycol and/or polyethylene glycol. If desired, such liquid preparations may contain colouring agents, flavouring agents, saccharine and carboxymethyl cellulose or other thickening agents. Liquid preparations for oral administration may also be prepared in the form of dry powder to be reconstituted with a suitable solvent prior to use.

For topical administration, NAC and/or SeMet and/or Mel may be applied in pure form, i.e. as liquids. In exemplary embodiments, they are administered in compositions/formulations comprising a dermatologically acceptable carrier, which may be a solid or a liquid, i.e. as an emulsified cream, ointment, lotion, liniment, powder or the like. Examples of liquid carriers include water, alcohols or glycols or water-alcohol/glycol blends, in which the present compounds can be dissolved or dispersed at effective levels, optionally with the aid of non-toxic surfactants. Thickeners such as synthetic polymers, fatty acids, fatty acid salts and esters, fatty alcohols, modified celluloses or modified mineral materials may be added to form ointments, lotions, pastes, gels and the like. Examples of solid carriers include finely divided solids such as talc, clay, microcrystalline cellulose, silica, alumina and the like. Adjuvants such as fragrances and additional antimicrobial agents may also be added. In an exemplary embodiment, a galenic formulation for topical administration comprises Aqua, Ceteareth 25 Glyceryl Stearate, Tea Stearate, Cetearyl alcool, Caprylic/Capric Triglyceride, Dimethicone, Glyceryn Hydrogenated Polyisobutene, Polysorbate 60, Pentylene Glycol and optionally vanilla.

For intravenous or intraperitoneal administration, solutions of the active compounds can be prepared in water, optionally mixed with a nontoxic surfactant. Dispersions can also be prepared in glycerol, liquid polyethylene glycols, triacetin, and mixtures thereof and in oils, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many embodiments, isotonic agents, for example, sugars, buffers or sodium chloride, are included. Prolonged absorption of the injectable compositions can be brought about by the use in the compositions of agents delaying absorption, for example, aluminum monostearate and gelatin. Sterile injectable solutions are prepared by incorporating the active compounds in the required amount in the appropriate solvent with various of the other ingredients enumerated above, as required, followed by filter sterilization. In the case of sterile powders for the preparation of sterile injectable solutions, in some embodiments, the methods of preparation are vacuum drying and the freeze drying techniques, which yield a powder of the active ingredient plus any additional desired ingredient present in the previously sterile filtered solutions.

Dosage units for rectal administration may be prepared in the form of suppositories which contain the active substances mixed with a neutral fat base, or they may be prepared in the form of a gelatin rectal capsule which contains the active substances in a mixture with a vegetable oil, paraffin oil or other suitable vehicle for gelatin rectal capsules, or they may be prepared in the form of a ready-made micro enema, or they may be prepared in the form of a dry micro enema formulation to be reconstituted in a suitable solvent just prior to administration.

Solutions for parenteral administration may be prepared as solutions of the active ingredients of the present disclosure in pharmaceutically acceptable solvents, such as in a concentration from 0.1 to 10% by weight. These solutions may also contain stabilizing agents and/or buffering agents and may be manufactured in different unit dose ampoules or vials. Solutions for parenteral administration may also be prepared as dry preparations to be reconstituted with a suitable solvent extemporaneously before use.

With regard to NAC, the present disclosure typically requires a strict assessment of the pharmaceutical quality of NAC preparation for obtaining the effective dose. NAC is not a stable molecule, its active thiol residue can be easily oxidized by oxygen, light and other radiations, so that the effective dose would not be reached. In various embodiments, the preparation is thus protected from light. For oral administration, NAC can be prepared in soluble tablets with sodium hydrogen carbonate, which helps in a partial removal of oxygen from water during dissolution.

It has been observed that high doses of NAC may cause abdominal pain. For overcoming this, an option is to provide NAC in a formulation with gastric protection, suitable for preventing NAC release/solubility in the stomach. Such formulations are well known in the art and may be used with the present disclosure. For example, tablet coatings that are resistant to gastric fluids and allow release of the drug only in the intestine, after its transit through the stomach, may be used. Commonly used formulations include polymers such as cellulose derivatives or methacrylate amino ester copolymers. The coating protects the tablet core from disintegration in the acidic environment of the stomach by employing pH sensitive polymer, which swell or solubilise after having passed through the stomach, in response to an increase in pH, to release the drug.

Dosages

For oral administration to a human, as well as other mammals, a suitable daily dose of NAC is approximately 5 and 45 mg/kg/day, such as 20-30 mg/kg/day. A suitable daily dose of SeMet is approximately 0.0004-0.0012 mg/kg/day, such as approximately 0.0008 mg/kg/day, and a suitable daily dose of Mel is approximately 0.02-0.08 mg/kg/day, such as approximately 0.04 mg/kg/day. The dose may be given once a day or may be divided in two or more, for example three or four, daily administrations of either one or two doses (e.g. pills) each, where each dose may comprise e.g. 0.15-3.0 g of NAC, for example 0.3-0.6 g of NAC and for example three times a day; 0.028-0.110 mg of SeMet such as approximately 0.055 mg of SeMet; and 1-6 mg of Mel such as approximately 3 mg of Mel.

For oral administration, the daily dosage weight ratio of NAC to SeMet is within the range of 4000:1 to 60 000:1, for example within the range of 5000:1 to 40 000:1 or 25 000:1 to 37 000:1, such as 32 500:1. The daily dosage weight ratio of NAC to Mel is within the range of 60:1 to 2000:1, for example 150:1 to 1000:1 or 500:1 to 750:1, such as 600:1. Typically the three substances are administered at a daily dosage weight ratio of NAC to SeMet to Mel that is approximately 32 500:1:54. The substances may be administered simultaneously, separately or in a composition comprising all three substances, in said ratios.

For epicutaneous administration (e.g. by emulsion cream, ointments, lotions, liniments or similar) a suitable concentration of NAC is approximately 3-10 wt-%, for example 5 wt-%. A suitable concentration of SeMet is approximately 0.3-1 wt-%, for example 0.5 wt-%, and a suitable daily dose of Mel is approximately 0.01-0.2 wt-%, for example 0.1 wt-%. The cream, lotion or similar may be applied once a day or may be applied in two or more, such as three or four, daily administrations.

For epicutaneous administration, the weight-% ratio of NAC to SeMet is within the range of 3:1 to 33:1, for example approximately 10:1. The weight-% ratio of NAC to Mel is within the range of 15:1 to 1000:1, for example approximately 50:1. Typically, the three substances are epicutaneously administered at a weight-% ratio of NAC to SeMet to Mel that is approximately 50:1:5. The substances may be administered simultaneously, separately or in a composition comprising all three substances, in said ratios.

Periods of treatment may last for one or a few days up to several months, depending on the disease or condition to be treated.

For longer periods of treatment with NAC and SeMet and Mel, e.g. 1-2 months or more, the treatment may be intermittent. By "intermittent administration or treatment" is meant that the treatment is interrupted in periods, i.e. that the pharmaceutical composition is administered for a period of time, e.g. a few days, followed by an interruption in administration, where no pharmaceutical composition is administered for a period of time, e.g. for a few days, and then followed by administration again. Intermittent treatment can be regular, e.g. treatment for a fixed number of days or weeks, followed by interruption for a fixed number of days or weeks. Examples include repeated schemes with treatment for 4 days followed by interruption for 3 days each week or treatment for 2 weeks followed by interruption 1 week. A special case of regular intermittent treatment is pulsed treatment, i.e. with regular treatment and interruption duration, e.g. administration every other day or administration for two days followed by two days of interruption etc. Irregular intermittent treatment schemes that are not regularly repeated or have a more complex scheme that is repeated is also conceivable, e.g. dependent on response to treatment. In different exemplifying embodiments of the present disclosure, the prescribed dose of NAC and SeMet and Mel is administered for 3-5 consecutive days followed by 2-4 days of interruption, or administered for 1-3 consecutive days followed by 1-2 days of interruption.

The dose of NAC, SeMet and Mel will depend on the particular formulation selected, the route of administration, the nature of the disease or condition to be treated as well as the weight, age, condition and species (human or animal) of the patient.

A known dose of NAC to treat a particular disease or condition may typically be approximately halved when NAC is administered together with the optimal dosages of SeMet and Mel. As an example, NAC for the treatment of endometriosis is in an embodiment, administered alone at a dose of 20-90 mg/kg/day, such as 30-60 mg/kg/day, orally, for two months or more. When NAC is administered in combination with SeMet and Mel the NAC dosage can be lowered to 15-30 mg/kg/day for two months or more.

Use/Medical Indications of the Present Disclosure

The present disclosure, comprising a combination of NAC, Se as selenomethionine and Mel, may be used for any purpose where NAC may be used or is known to have an effect, e.g. in diseases where glutathione is involved and/or in which thiol (—SH) reduction/oxidation (redox) switches play a fundamental role, as in the case of signaling, also driven by hormones, or where NAC's antiproliferative and prodifferentiating effect, antioxidant or antiinflammatory effects may be utilized. It may for example be used for the treatment of benign and malignant neoplasia, including various types of cancers, type 2 diabetes, various types of fibrosis, endometriosis, polycystic ovary syndrome, dysmenorrhea and dermatological diseases, including vitiligo and psoriasis, and anxiety disorders, including sleep disorder and fatigue. Due to the relevance of oxidation phenomena in protein aggregation to form amyloids, the present disclosure can be used for the prevention and treatment of various types of amyloidosis, such as Alzheimer's disease. In addition, it may be used as an antibacterial agent and for cosmetic purposes. Other uses also include treatment of HIV/AIDS, chemical and infectious hepatitis, cataracts, Parkinson's disease, chronic obstructive pulmonary disease, asthma, radiation poisoning, malnutritive states, arduous physical stress, aging, sepsis, trauma, burns, bipolar disorder, major depressive disorder, and schizophrenia, and for patients with suboptimal immune response.

Figure 2:
FIG. 2 shows the effect of a three months treatment with NAC+SeMet+Mel on a patient with vitiligo, as described in Example 1.

As an example of treatment of dermatological diseases, one patient with vitiligo was treated with the combination of the three substances and after three months of treatment an extreme reduction of depigmentation was observed (Example 1, FIG. 2).

As an example of cosmetic treatment, skin texture on a subject whose face skin was treated for one month with a galenic preparation containing the three compounds, was monitored. After one month of combined treatment with a cream preparation containing NAC, SeMet and Mel, face surface lines appeared more regular, the skin appeared more compact and smoother and skin irregularities and pimples were reduced.

Combination of NAC, SeMet and Mel for Use as an Antibacterial Agent

The present inventors also show (Example 5) that the combination of NAC, SeMet and Mel is effective for use as an antibacterial agent, e.g. when comprised in a coating on medical instruments and devices such as catheters of latex or polyvinyl chloride. Alternatively, the combination of NAC, SeMet and Mel may be incorporated in plastic materials for use in medical devices.

For instance, hydrogel coating may be used as a method for solid substrate surface modification. Examples of hydrogel coatings include water insoluble hydrogel based on polyurethane (PUR) or polyvinylpyrrolidone (PVP). Besides advantages like improving material biocompatibility, hydrophilization and lubrication, hydrogel coating brings the additional possibility of incorporating active agents to the surface, e.g. NAC, SeMet and Mel. Combinations of a hydrophilic matrix and a hydrophobic drug composition of NAC, SeMet and Mel seem to be especially promising.

Hydrogel modified surfaces have the additional advantage over unmodified surfaces, in that they can serve as a drug reservoirs for a local drug delivery. For example, in certain circumstances drug dosage time should last at least a few hours, but no longer than 3 days. It can be desirable e.g. in case of implantation of devices like tracheotomy tubes, when anti-inflammatory active substances should be released at the very beginning, to prevent later side effects like tracheal stenosis, but later should not interrupt normal cell divisions in the subsequent healing process and epithelium formation. By using a hydrophilic hydrogel matrix with hydrophobic NAC, SeMet and Mel, this release profile can easily be obtained due to the properties of the hydrophilic matrix as controlled drug release system during its swelling.

In addition to NAC, SeMet and Mel, further active substances may be added to coatings or plastics for use with medical instruments and devices, e.g. germicidal drugs, noble metal solutions and/or dexamethasone.

The active agent, i.e. NAC, SeMet and Mel, and possibly one or more additional active substance(s) may be incorporated to the coating in two different modes: I. as a component of the solution in any step of the coating formation, e.g. during polymerization of the hydrogel coating, or II. through an impregnation bath. The later mode II. is in one embodiment, made as an additional step after formation of a hydrogel coating, but may also be done without such coating, directly to the medical device. Mode II. allows for modification of devices like silicone catheters or polyglycolic acid resorbable sutures without polymeric coating step or with the addition of the active substances subsequent to the polymeric coating step.

The effects of active agent incorporation have been verified by the present inventors through drug dissolution tests to the phosphate buffered saline (PBS) S) with 20% methanol or ethanol, extraction, and, in case of germicidal drug, by the inhibited growth zones method (data not shown). The dependency of the rate of drug dissolution and the load capacity, as well as coating stability on the process parameters were investigated. The present inventors observed a spreading effect of NAC, SeMet and Mel during hydrogel swelling, as solid microparticles of the substances (NAC, SeMet, Mel) were precipitated out of the coating layer to the surrounding solution.

The present inventors show (Example 5) that the use of hydrogel coatings comprising NAC, SeMet and Mel on catheter material (polyvinyl chloride, latex) significantly reduce the growth of bacteria as well as the formation of bacterial biofilms on such material, compared to both non-coated backbone material and hydrogel coated material without NAC, SeMet and Mel.

EXAMPLES

Example 1: Treatment of Vitilgo

Vitiligo is an acquired pigmentation disorder in which there is a loss of skin melanocytes. As a result, white patches appear on the skin in different parts of the body. The prevalence of vitiligo varies in the range of 0.1-2% worldwide. Vitiligo can be psychologically devastating for the affected patient and can affect quality of life, self-esteem, marriage, and employment (Halder R M, Chappell J L. Semin Cutan Med Surg. 2009; 28(2):86-92.). The precise pathogenesis remains elusive, with proposed mechanisms falling under the rubrics of autoimmune, biochemical, oxidant-antioxidant, neural, and viral. Several studies suggest that accumulation of free radicals toxic to melanocytes leads to their destruction. Indeed, compared with control patients, the red cells of vitiligo patients have lower levels of glutathione.

In the present example, we report the case of a 45 year old woman with diffuse vitiligo around her neck and in both armpits. She was treated for three months using the following commercially available drugs, in the form of tablets taken orally, with the protocol: 0.6 g NAC, three times/day; SeMet, 55 micrograms/once a day; Mel, 3 mg/once a day; all the three drugs for the same three days/week followed by 4 days of interruption (no administration).

Pictures of her neck and both armpits were taken at the beginning and at the end of the three months treatment.

No adverse side effects were reported.

From the pictures in FIG. 2, a clear reduction in depigmentation is evident, with an almost complete repigmentation in both armpits.

Example 2: Cosmetic Treatment of Skin

Ageing of the skin can be macroscopically recognized because of wrinkles, loss of elasticity, sagging and thinning which take place gradually in the adult. Therefore, determination of skin surface texture is of particular importance in the field of dermatology as such measurements can be used for skin diagnostics and evaluation of therapeutic or cosmetic treatments.

Of increasing relevance is the impact of environmental pollution on skin, often degraded by polluting agents with the associated ageing and dysfunctions. Skin is directly exposed to pollution with an individual surface evaluated of about 2 square meters, larger than any other human tissue. Mechanisms for damages due to pollution mainly resides in the induction of oxidative stress and inflammatory response. These mechanisms drive us to the use of NAC, in combination with SeMet and Mel, in a case of mildly aged, oily skin, with pimples.

A 43 year old woman visited a dermatologist for her oily skin, presenting redness and pimples. She was treated for one month with a galenic preparation containing: Aqua, Ceteareth 25 Glyceryl Stearate, Tea Stearate, Cetearyl alcohol, NAC 5%, SeMet 0.5%, Mel 0.1%, Caprylic/Capric Triglyceride, Dimethicone, Glyceryn Hydrogenated Polyisobutene, Polysorbate 60, Pentylene Glycol, and vanilla.

Figure 3B:
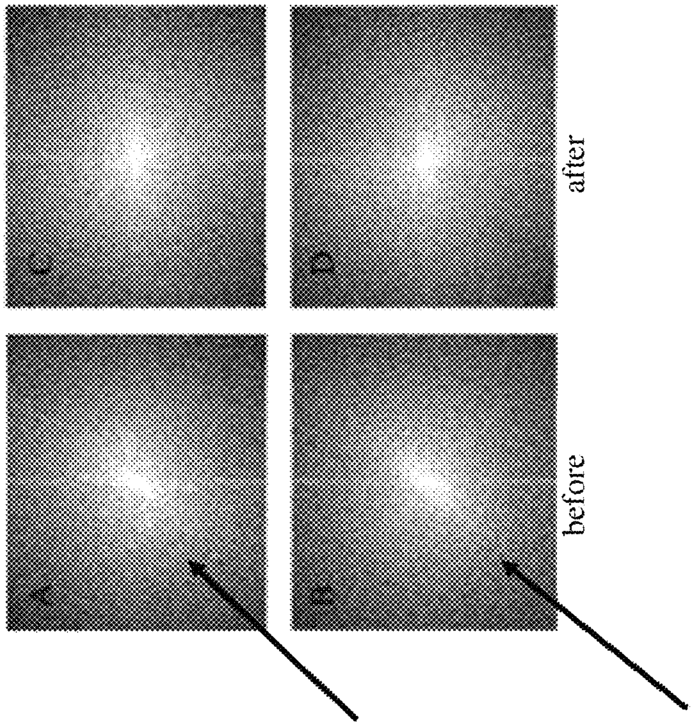
FIG. 3B shows the Fast Fourier transform (FFT) of some of the images in FIG. 3A showing an irregular pattern prevalent in a single direction in the samples before treatment (A and B), while a regular circular pattern is observed after treatment (C and D).
Figure 3A:
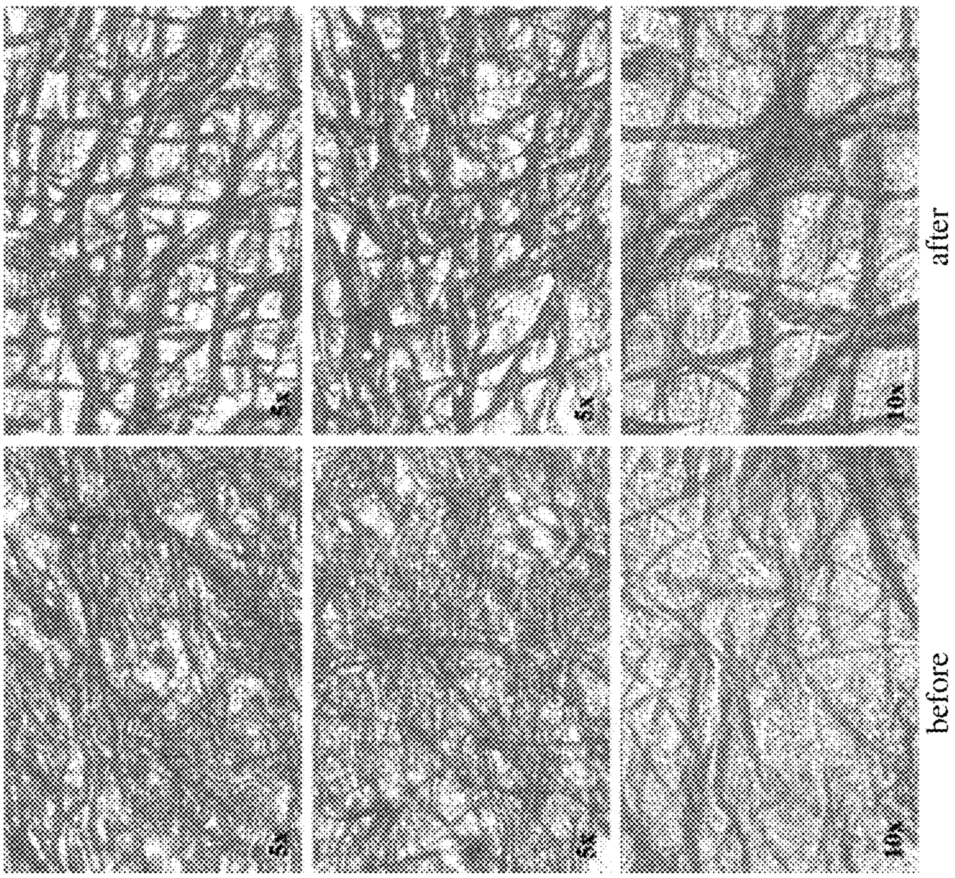
FIG. 3A shows the effect on skin texture of a one month treatment with NAC+SeMet+Mel, as described in Example 2. Microscopy images of silicon rubber skin replicas showing a network of thin lines characterizing the microrelief of skin surface. Note the more regular network after treatment. Magnification: 5× or 10×, as reported in the panels.

Skin texture was evaluated on silicon rubber skin replicas, prepared by the dermatologist then observed by microscopy (FIG. 3A), following a reported procedure (Setaro M, Sparavigna A. Irregularity skin index (ISI): a tool to evaluate skin surface texture. Skin Res Technol. 2001; 7(3):159-63.). As illustrated by these authors, through the analysis of surface lines, microscopy of skin replicas shows the variation in regularity of skin surface texture. After one month of combined treatment with a cream preparation containing NAC, SeMet and Mel, the face surface lines appeared more regular, with an impressively increased order in their network, particularly when compared with the random coiled appearance observed before the treatment. The Fast Fourier transform (FFT) analysis of the images, performed following the method of Setaro and Sparavigna, indeed showed (FIG. 3B) a pattern with a preferential direction before the treatment—as indicated by the arrows in the left panels A and B, indicating an irregular texture. After the treatment, the FFT analysis showed instead an almost completely regularly circular pattern, indicating a regular skin texture.

After the month of treatment, both the dermatologist and the patient reported a visual decrease in skin irregularities with a more compact and smoother appearance, a normalization of the sebaceous secretion, and the disappearance of redness and pimples.

Example 3: Antioxidant Effect on In Vitro Cultured Blastoid Cell Lines

Methods

The human lymphoblastoid HL60 and the proerythoblastoid K562 cell lines were used, grown at 37° C. in RPMI 1640 medium (Invitrogen, Gibco, Milano, Italy), supplemented with 10% fetal bovine serum, 5 μg/ml penicillin, 5 μg/ml streptomycin, 2 mM glutamine, and routinely subcultured three times a week. Cells were treated either with menadione alone (control), with NAC only, with NAC+Se-methionine (SeMet), with NAC+Mel, or with NAC+SeMet+Mel. In cases of SeMet supplementation, such supplementation was performed two days before experiments, by using a SeMet solution in buffer (concentrations as indicated in description of FIGS. 4-7). In cases of Mel supplementation, such supplementation was performed 20 hours before experiments, by using a solution in ethanol (concentrations as indicated in description of FIGS. 4-7). Ethanol concentration in growth medium was <1.3% and controls only with this solvent were also grown in parallel.

The effect of NAC, Mel, SeMet and of a combination of these substances in protecting the cells against an oxidative stimulus was detected by using the fluorescent probe 5-(and- 6)-chloromethyl-2',7'-dichlorodihydrofluorescein diacetate, acetyl ester (CM-H2DCFDA) (Invitrogen, Molecular Probes). CM-H2DCFDA is a cell-permeant indicator for reactive oxygen species that is not fluorescent until removal of its acetate groups by intracellular esterases, and oxidation within the cell. The increase in hydroperoxides (mainly $H_2O_2$) within the cell is thus monitored by increase in fluorescence. Oxidative stimulus for the increase in $H_2O_2$ was performed by using menadione.

Cells were counted, and care was taken to keep the ratio between cells and the fluorescent probe constant. Washed cells were resuspended in 2 ml HBSS at a concentration of $10^6$/ml, then transferred to a cuvette and equilibrated at 37±0.1° C. in the fluorimeter cell holder for 15 min, under mild stirring. Two µl of a solution of CM-H2DCFDA in DMSO were then added and the fluorescence intensity read versus time. After the first 200 sec of reading, a proper aliquot of NAC solution in phosphate buffer (concentrations as indicated in description of FIGS. 4-7), and 10 µl of a 0.1 M solution of menadione in ethanol were added, and the fluorescence intensity reading continued. During intensity readings, samples were subjected to continuous mild stirring.

The fluorescence intensity was continuously monitored for 20 min in a K2 fluorimeter (ISS Inc. Champaign, IL) equipped with a xenon arc lamp, by using excitation at 495 nm and emission at 530 nm, with 8 nm bandpass.

Results

Figure 4:
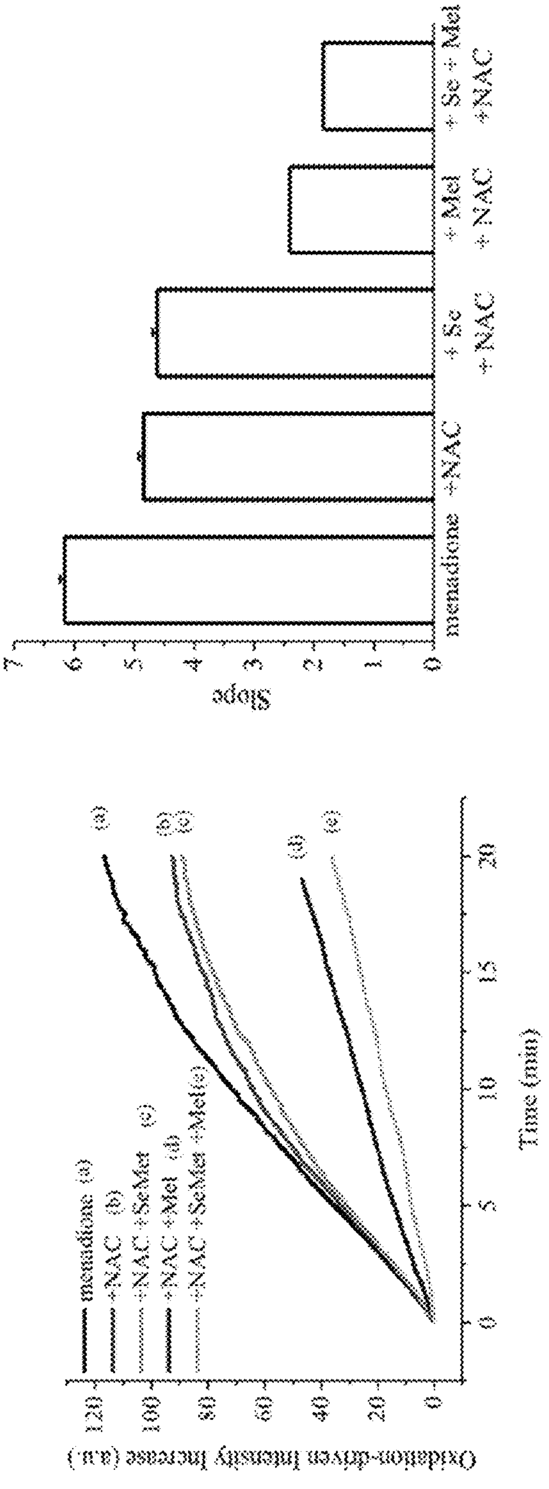
FIG. 4 shows results from experiments described in Example 3. K562 cells were treated with 0.2 mM menadione and/or 0.4 mM NAC and/or 0.2 mM SeMet and/or 2 mM Mel as indicated. In the histogram, the indication Se always refers to SeMet.
Figure 5:
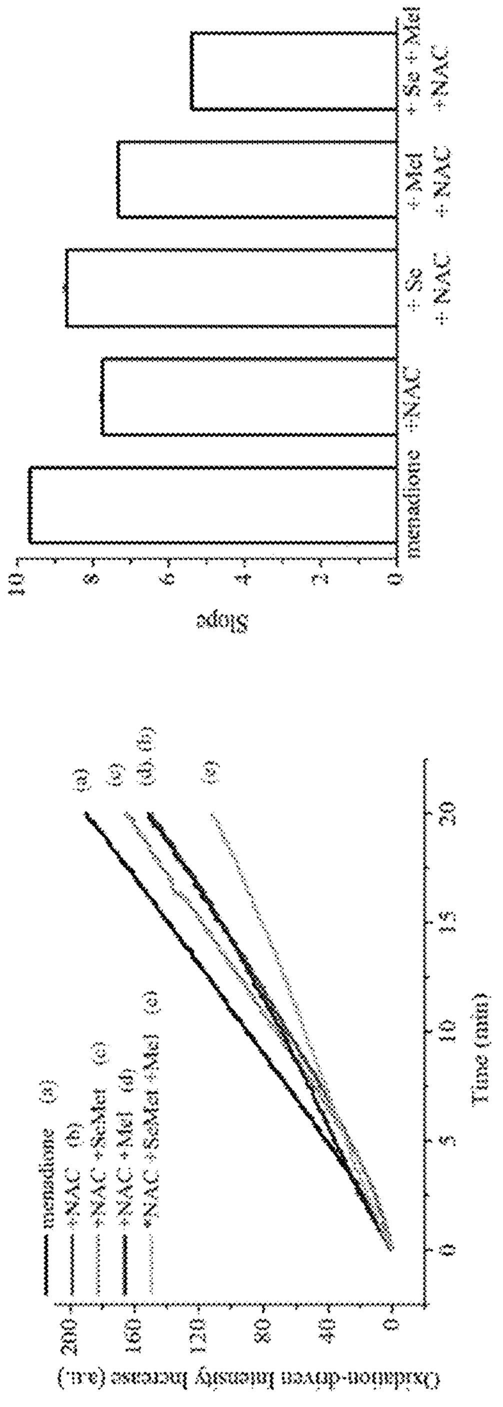
FIG. 5 shows results from experiments described in Example 3. HL60 cells were treated with 0.133 mM menadione and/or 0.4 mM NAC and/or 0.2 mM SeMet and/or 2 mM Mel as indicated. In the histogram, the indication Se always refers to SeMet.
Figure 6:
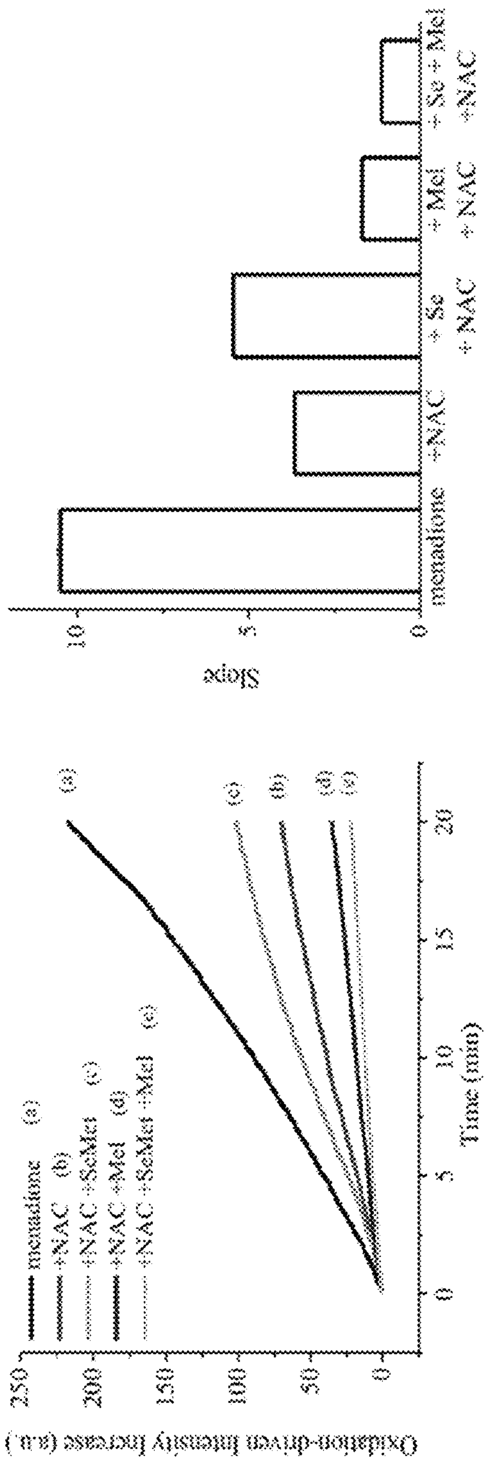
FIG. 6 shows results from experiments described in Example 3. HL60 cells were treated with 0.5 mM menadione and/or 1 mM NAC and/or 0.2 mM SeMet and/or 1 mM Mel as indicated. In the histogram, the indication Se always refers to SeMet.

Representative results of the oxidative response in the cells after the respective treatment are shown in FIGS. 4, 5 and 6. Different concentrations of menadione, NAC, SeMet and Mel were tested and gave different responses, also depending on the cell line. Nevertheless, the combination of the three substances always resulted as the most effective in preventing the oxidation-driven increase in fluorescence. After the oxidative challenge with menadione, the DCFDA fluorescence intensity increased. NAC addition resulted in a relevant reduction in the kinetics of this intensity increase, as evaluated by its slope. The presence of either SeMet or Mel together with NAC had different effects depending on the cell type and on concentration.

Notably, in some cases it was observed that the couples NAC+SeMet or NAC+Mel, instead of decreasing the response, accelerated the fluorescence increase, thus suggesting a pro-oxidant effect. A representative example is reported in FIG. 6. Nevertheless, even in these cases the combination of the three components, NAC+SeMet+Mel, resulted in the maximum decrease in the slope, and thus of the oxidative response, relative to the control.

Figure 7:
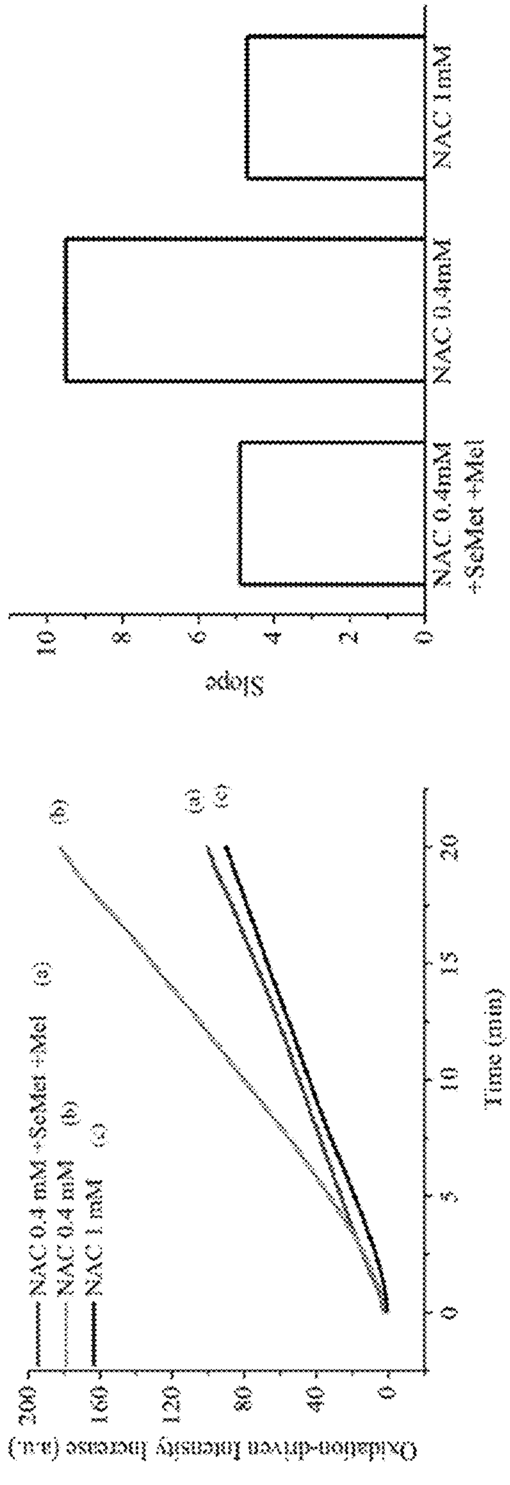
FIG. 7 shows results from experiments described in Example 3. HL60 cells were treated with 0.133 mM menadione, 0.2 mM SeMet, 2 mM Mel and different NAC concentrations as indicated.

The powerful antioxidant defense operated by the combination of NAC+SeMet+Mel allowed a 60% reduction in NAC concentration. This is shown in FIG. 7 where the protection exerted by 1 mM NAC is comparable to that obtained by using only 0.4 mM NAC in combination with SeMet and Mel.

Conclusions

The combination of NAC with SeMet and Mel definitely increases the antioxidant defense of NAC. The combination exerts a synergistic effect, not only with regard to NAC action but also with regard to the action of each of the three components alone. In relation to NAC alone, in several cases the antioxidant effect was three times as effective when NAC was used in combination with SeMet and Mel.

NAC concentration could be decreased, a similar effect being reached using less than half of the concentration.

Surprisingly, in some cases, an unfavorable pro-oxidant effect of SeMet or of Mel, also in combination with NAC, was observed. Although the mechanisms are still debated, adverse pro-oxidant effects were reported in the literature both for Se and for Mel. Nevertheless, in our experiments the combination of the three substances, wherein Se is in the form of SeMet, restored an antioxidant cell protection, with a final effect of negligible oxidation even after the oxidant challenge.

Example 4: Differentiating Effect in Colon Carcinoma Cells

NAC was previously reported to modulate cell proliferation and differentiation, specifically to reduce proliferation by switching cells towards a normal differentiation pathway. Reportedly, this action occurs in normal cells as well as in cancer cells.

Figure 8:
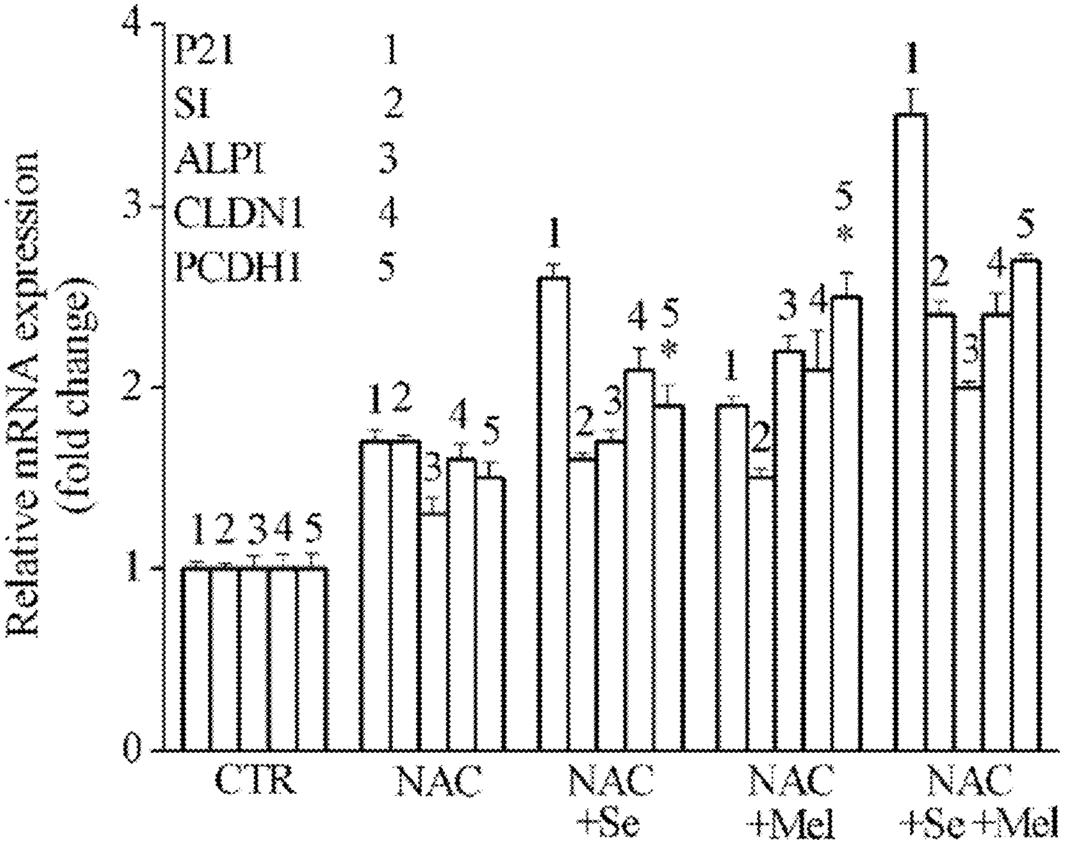
FIG. 8 shows results from experiments described in Example 4, demonstrating the antiproliferative and differentiating action of NAC in combination with SeMet and Mel. Average fold changes of the inhibitor of proliferation gene P21 (average of 5 exps.) and of the differentiation markers SI (5 exps.), ALPI (4 exps.), CLDN1 (6 exps.) and PCDH1 (5 exps.). Significance, $p<0.05$, excluding two samples marked with (*) where the combination NAC+Se and NAC+Mel were not significantly different from that of NAC+SeMet+Mel. In the histogram, the indication Se always refers to SeMet.
Figure 9:
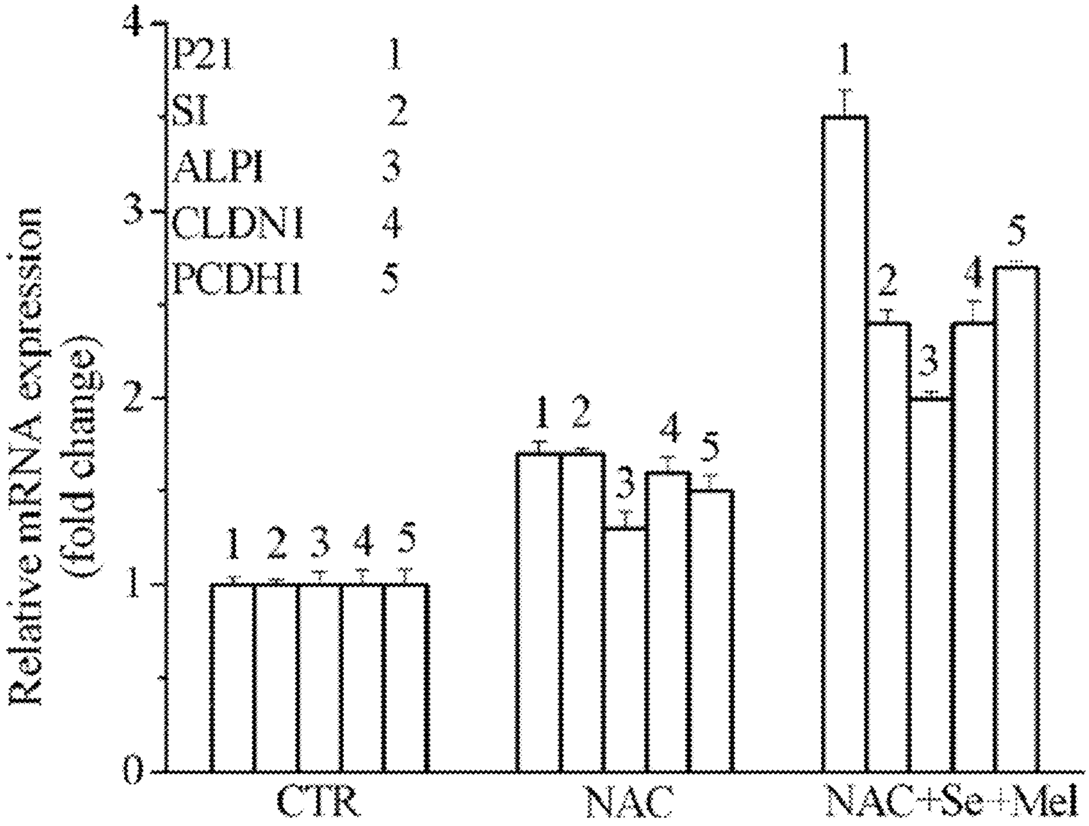
FIG. 9 shows a comparison of the effect of NAC alone with the combination of the three substances. In the histogram, the indication Se always refers to SeMet.

The expression of genes related to proliferation and differentiation in a colon carcinoma cell line (Caco-2) treated with NAC, in combination with SeMet or Mel or both, was analyzed as below. Results are shown in FIGS. 8 and 9.

Methods

The colon carcinoma cells Caco-2 (subclone TC7, Chantret et al., J. Cell Sci. 107:213-225; 1994) were routinely maintained in high glucose DMEM (Gibco, Invitrogen, Milan, Italy) containing 10% heat-inactivated fetal bovine serum, FBS (Gibco, Invitrogen). Cells were seeded at a density of $3\times10^3$/cm$^2$ on six-well plates. 24 h after seeding cells were treated with NAC (2 mM) and/or SeMet (25 nM) and/or Mel (25 After 72 hours of treatment, cells were analyzed for gene expression.

Expression of genes characteristic of enterocyte differentiation was evaluated; two genes encoding for brush border hydrolases, the intestinal alkaline phosphatase (ALPI) and the sucrase-isomaltase alpha-glucosidase (SI); two genes encoding for proteins of cell-cell adhesion complex, the tight junction claudin 1 (CLDN1) and the adherent junction protocadherin 1 (PCDH1). The expression of an important inhibitor of cell cycle, the cyclin-dependent kinase inhibitor 1A (CDKN1A/$P21^{waf1/cip1}$) as a marker of cell cycle arrest that normally accompanies Caco-2 cell differentiation was also analyzed. Glyceraldehyde-3-phosphate dehydrogenase (GAPDH) was used as housekeeping gene.

Specific primer sequences were designed using the software Primer-BLAST available at: http://www.ncbi.nlm.nih.gov and are reported in Table 1.

Total RNA was extracted in TRIzol Reagent (Invitrogen). One microgram of total RNA from each sample was treated with 1U of DNAse I (Invitrogen) and reverse transcribed with 200U of SuperScript III Reverse Transcriptase (Invitrogen), using 250 ng of random primers in 20 µl (final volume). Real-time quantitative RT-PCR was performed on ABI Prism 7000 (Applied Biosystems, Monza, Italy) using the 5 Prime RealMasterMix SYBR ROX 2.5× (Eppendorf, Milan, Italy) in a 25 µl reaction volume containing 10 ng of cDNA and 0.6 µl of each primer (10 µM), according to the following protocol: 1 cycle of 10 min at 95° C., 40 cycles of three steps including 20 sec at 95° C., 40 sec at 60° C., and 45 sec at 68° C. All experiments were performed as duplicate in three or more separate assays. A negative control (no template) was run with each reaction to verify the absence of contaminations, and the specificity of amplifications was confirmed by melting curve analysis. All data were analyzed as averages with standard error and significance was evaluated through the p parameter using ANOVA. For the determination of relative transcript abundance, the $2^{-\Delta\Delta CT}$ method was used (Livak K J, Schmittgen T D. Methods 2001; 25: 402-408.).

TABLE 1

| Target mRNA | Primers | SEQ ID NO: | DNA Sequence |
|---|---|---|---|
| SI | forward | 1 | ACGATGGGGAGGACACTGGCT |
| NM_001041.2 | reverse | 2 | TCCAAGTTGCATCCAGCGGGT |
| ALPI | forward | 3 | GTATGTGTGGAACCGCACTG |
| NM_001631.3 | reverse | 4 | CTGGTAAGCCACACCCTCAT |
| CLDN1 | forward | 5 | TGGCTGTCATTGGGGGTGCG |
| NM_021101.3 | reverse | 6 | GCAGCAGCCCAGCCAGTGAA |
| PCDH1 | forward | 7 | CCTATCCAGCCTGAGCTTTG |
| NM_002587.3 | reverse | 8 | GGCAGTGATATAGGGTGCGT |
| P21/cdkn1a | forward | 9 | TGAGCTGCGCCAGCTGAGGT |
| NM_000389.3 | reverse | 10 | GCTGCTCGCTGTCCACTGGG |
| GAPDH | forward | 11 | GTCAGTGGTGGACCTGACC |
| NM_002046.3 | reverse | 12 | AGGGGTCTACATGGCAACTG |

Results

Results are shown in FIGS. 8 and 9, showing the increase (fold change) in gene expression of the five genes, when cells are subjected to the respective treatment. The real-time quantitative RT-PCR data undoubtedly show that:

1) the antiproliferative action of NAC (as indicated by an increased expression of the P21 gene) is doubled by the combination with SeMet and Mel, as compared to NAC alone.
2) the differentiating action of NAC (as indicated by an increased expression of the marker genes SI, ALPI, CLDN1, PCDH1) is definitely enhanced by the above combination, with marker genes expression being 40-80% higher, as compared to NAC alone.
3) although, when analyzing some specific differentiation markers, for instance ALPI, CLDN1 and PCDH1, it was observed that the couple combinations NAC+SeMet or NAC+Mel had an effect that is comparable to the combination of the three substances, there is nevertheless a clear trend to an overall increased induction of differentiation when the three substances are used in combination.

Example 5: Antibacterial Effect of NAC, SeMet and Mel in Hydrogel Coatings of Medical Devices Methods Hydrogel Coating:

A method as known in the art for polymer coating of water insoluble hydrogel, based on polyurethane (PUR) and polyvinylpyrrolidone (PVP), designed for medical polymeric devices, was used to coat urethral poly vinyl chloride catheters as well as latex catheters. This hydrogel layer has previously been characterized by the means of the Fourier Transform Infra-Red Attenuated Total Reflection (FTIR-ATR) spectroscopy, static and kinematic friction factor relative to the uncoated backbone material and against porcine tissue counter-face, water wetting angle and microscopic observations. Tests made by the present inventors (data not shown) confirm changes in surface composition, superhydrophilicity and lubricity in hydrated state including friction factor reduction. In case of urethral poly vinyl chloride catheters with hydrogel coated inner surface, the capillary action phenomenon was observed, proving high affinity between coating and water molecules.

Bacterial Growth and Biofilm Formation:

To measure the effect on formation of adherent sessile bacteria an artificial catheter was constructed according to the technique described by Nickel and associates (Antimicrob Agents Chemother. 1985; 27(4):619-24). Catheter materials used were latex, latex coated with noble metal comprising hydrogel, latex coated with NAC, SeMet and Mel (NAC+SeMet+Mel) and latex coated with both noble metal and (NAC+SeMet+Mel). The artificial catheter device was connected to a two liter reservoir, functioning as an in vitro bladder held in 37° C. water bath. Medium containing *Escherichia Coli* (*E. coli*) was pumped from the reservoir through the artificial catheter by a pump set to deliver 50 ml/h. 10 $cm^2$ of the midsection of the catheter was tested before and after exposure to the *E. coli*. The strain of *E. coli* used in these experiments was isolated from a patient with catheter associated urinary tract infection. The medium used was artificial urine supplemented with 0.4% nutrient broth. The bacteria were stored on a sloping agar in a test tube (slants) at −70° C. and serially cultured at 10 h intervals. Bacterial growth within the in vitro bladder was monitored by using standardized turbidity as a growth parameter with a spectrophotometer at 600 nm.

Artificial urine containing *E. coli* was passed through the artificial catheter for 10 h and the development of bacterial biofilm was monitored by sampling of catheter material surfaces. Sample discs bearing sessile bacteria were aseptically removed for scanning electron microscopy. Also, quantitative counts of viable adherent bacteria were obtained by low-output ultrasonication of surface scraping of the catheter disc in a sterile phosphate-buffered saline solution. Dilution series were made up to $10^{-4}$ and spread on nutrient agar from which quantitative plate counts were obtained. The catheter specimens designated for SEM were removed from the artificial catheter and placed in fixative solution consisting of 5% glutaraldehyde in cacodylate buffer (0.1 M, pH7.2) for 1 h at 22° C., followed by dehydration in a series of aqueous ethanol solutions (20-100% and Freon 113-ethanol solutions (30-100%) and then air dried. Samples were coated with gold in a sputter coater and examined by using a scanning electron microscope.

Results

The growth on nutrient agar of surface scrapings of the catheter disc revealed that the number of viable *E. coli* was significantly decreased on hydrogel coated material compared to uncoated backbone material. A further dramatic decrease in the number of adhered bacterial colonies was noted when adding NAC, SeMet and Mel to the hydrogel.

Number of colonies on the backbone material: 100

Number of colonies on the hydrogel coated material: 73

Number of colonies on the hydrogel with NAC, SeMet and Mel coated material: 58

Examination by SEM showed that the discs of catheter latex, noble metal coated latex, (NAC+SeMet+Mel) coated latex, and noble metal+(NAC+SeMet+Mel) coated latex did not bear significant numbers of ethanol killed bacterial cells before exposure to *E. coli*. Ten minutes after exposure to cells of *E. coli* in artificial urine, significant numbers of adherent bacterial cells were seen on the latex discs whereas there was minimal colonization on the noble metal coated latex or (NAC+SeMet+Mel) coated discs and no colonization on the noble metal+(NAC+SeMet+Mel) coated discs. After 10 h of colonization, the characteristic plate-like surface of the uncoated latex discs was completely occluded by a large number of adherent bacteria, which were embedded in large amounts of their own amorphous exopolysaccarides to form a thick adherent biofilm. On the noble metal coated catheter discs and on the (NAC+SeMet+Mel) coated catheter discs there were sparse signs of biofilm formation whereas there was no biofilm on the discs coated with the combination of noble metal and (NAC+SeMet+Mel).

Example 6: Effect of NAC, SeMet and Mel in the Treatment of Anxiety

Anxiety Definitions and Mechanisms

Anxiety has been defined as a state of high arousal and enhanced vigilance in the absence of an immediate threat. It is characterized by subjective experiences, such as persistent worry and tension, in addition to physiological changes, such as sweating and increased heart rate. Though healthy individuals may present sporadic anxiety, it becomes pathological if persistent, disruptive, and disproportionate. Anxiety disorders have global lifetime pre-valence rates as high as 28%, and include social phobia, panic disorder, agoraphobia, and generalized anxiety disorder (GAD). Though obsessive-compulsive disorders (OCD) and posttraumatic stress disorder (PTSD) present marked anxiety symptoms, the Diagnostic and Statistical Manual of mental disorders Fifth Edition (DSM-5) categorizes these conditions as obsessive-compulsive and related disorders, as well as trauma and stressor-related disorders, respectively.

In addition to drug therapy, the current treatment of anxiety disorders involves lifestyle interventions, such as physical exercise and mindfulness-based stress reduction, as well as psychological interventions, such as cognitive behavioral therapy, which are difficult to implement. The main drug classes used to treat anxiety disorders are GABAergic or serotonergic agents, including benzodiazepines (BZD), 5-HT1A serotonin receptor agonists, and selective serotonin reuptake inhibitors (SSRIs). Unfortunately, however, not all patients respond to the available medications. Moreover, BZDs and SSRIs are associated with unwanted adverse effects, including sedation, memory deficits, dependence, withdrawal syndrome, sexual dysfunction, and weight gain. While these adverse effects decrease adherence to treatment, the better-tolerated 5-HT1A agonist buspirone has the slowest onset of action and its efficacy is limited to GAD.

Despite its high prevalence, few effective therapeutic targets have been identified for anxiety disorders. The expectation that highly selective agents acting on specific molecular targets would yield better and safer psychiatric drugs has not yet been met. A newer approach involving multi-targeted agents recognizes the complex patho-physiology underlying psychiatric disorders. In anxiety disorders, oxidative stress, neuroinflammation, and glutamatergic hyperactivity are now recognized as key contributing factors.

For example, endometriosis as described herein is related to a range of psychiatric symptoms, especially depression, anxiety and psychosocial stress.

Method

In a method in accordance with embodiments of this disclosure a medical product comprising NAC, SeMet and Mel in accordance with embodiments was given to a plurality of groups of patients in the treatment of anxiety. The method of treating an anxiety disorder comprises administering to a patient in need thereof, a medical product consisting of one or more excipients and active agents consisting of (i) N-acetyl-L-cysteine; (ii) selenium in the form of selenomethionine; and (iii) melatonin and/or physiologically acceptable salts thereof.

In a trial the NAC, SeMet and Mel medical product, herein also called NAC-factor 3, was administered to the groups of patients in a set-up to compare the anxiolytic effect of placebo, NAC and the medical product consisting of NAC, SeMet and Mel in anxiolysis. The groups of patients were ordered according to the following different causes of anxiety: Sporadic anxiety (i.e. healthy patients) (SA), Social phobia (SP), Agoraphobia (AP), Panic disorder (PD), Generalized anxiety disorder (GAD), Obsessive-compulsive disorders (OCD), and Posttraumatic stress disorder (PTSD).

The patients rated their experienced intensity of pain from the anxiety before and after being exposed to medication with one of placebo, NAC and the medical product consisting of NAC, SeMet and Mel (in short NACSeMel), respectively. The subjective pain-intensity was rated by the patients using a 5 graded verbal rating scale ranging from None/Ignorable=0, Slight=1, Moderate=2, Great=3, Excruciating=4, where the corresponding numbers 0-4 are used to illustrate the responses in accompanying graphs.

In studying the results of the rating, the change in rating that the group delivered was expressed as a measure of the group's relative position RP in order to assess whether there was a systematic change in position on the rating scale. The relative position, i.e. the change in rating is negative if the rating indicates less pain intensity after exposure to treatment compared to before treatment, and positive if the rating indicates higher pain intensity after exposure to treatment. A range of values for the relative position RP was calculated for a 95% confidence interval CI.

Results

Placebo Comparison—Placebo, NAC, NACSeMel in Treatment of Anxiety

When a group composed of 20 patients suffering from varying kinds of anxiety were exposed to the placebo treatment, 7 of the 20 patients (35%) rated their pain-intensity lower, 4 of them (20%) rated higher and 9 (45%) of them rated the same pain-intensity after as compared to before placebo treatment. The change in the group may be expressed as the measure of the group's relative position, RP, as −0.10 (95% CI −0.37 to 0.18) and confirmed that there was no systematic change in position on the rating scale for pain intensity after treatment with Placebo compared to before treatment.

In the same group of patients, the change in rated pain-intensity after treatment with NAC showed that 8 patients (40%) rated lower, 5 patients (25%) rated higher, and 7 patients (35%) rated unchanged pain-intensity after treatment. The corresponding RP value for the group was −0.41 (95% CI −0.59 to −0.23) demonstrating a systematic change after treatment with NAC compared to before treatment.

The patients in the same group were also treated with NAC-factor 3/NACSeMel. Among the individuals there were 17 patients (85%) that responded with lower pain-intensity ratings and the rest 3 individuals (15%) rated the same pain-intensity after treatment as before treatment. For the change in position of the rating scale group the RP value was RP −0.65 (95% CI −0.81 to −0.49) and thereby stated a systematic change to lower levels of pain intensity on the rating scale after treatment with NACSeMel compared to before treatment.

These results are presented in the following Table 2, Table 3 and in FIG. 10. In Table 2, the Rated Variable is indicated as Varying kinds of anxiety, the total number of respondent patients is n=20 and there is a reference to an illustration of the data in a diagram in FIG. 10. The response rating data is indicated for Placebo, NAC, NACSeMel, respectively, with the following notation:

↓=number of patients that rated lower pain intensity after treatment,

↑=number of patients that rated higher pain intensity after treatment;

~=number of patients that rated unchanged level.

The value for the relative change RP is indicated for each treatment as well as the value range of RP values for a 95% confidence interval CI indicated within parentheses.

TABLE 2

Figure 10:
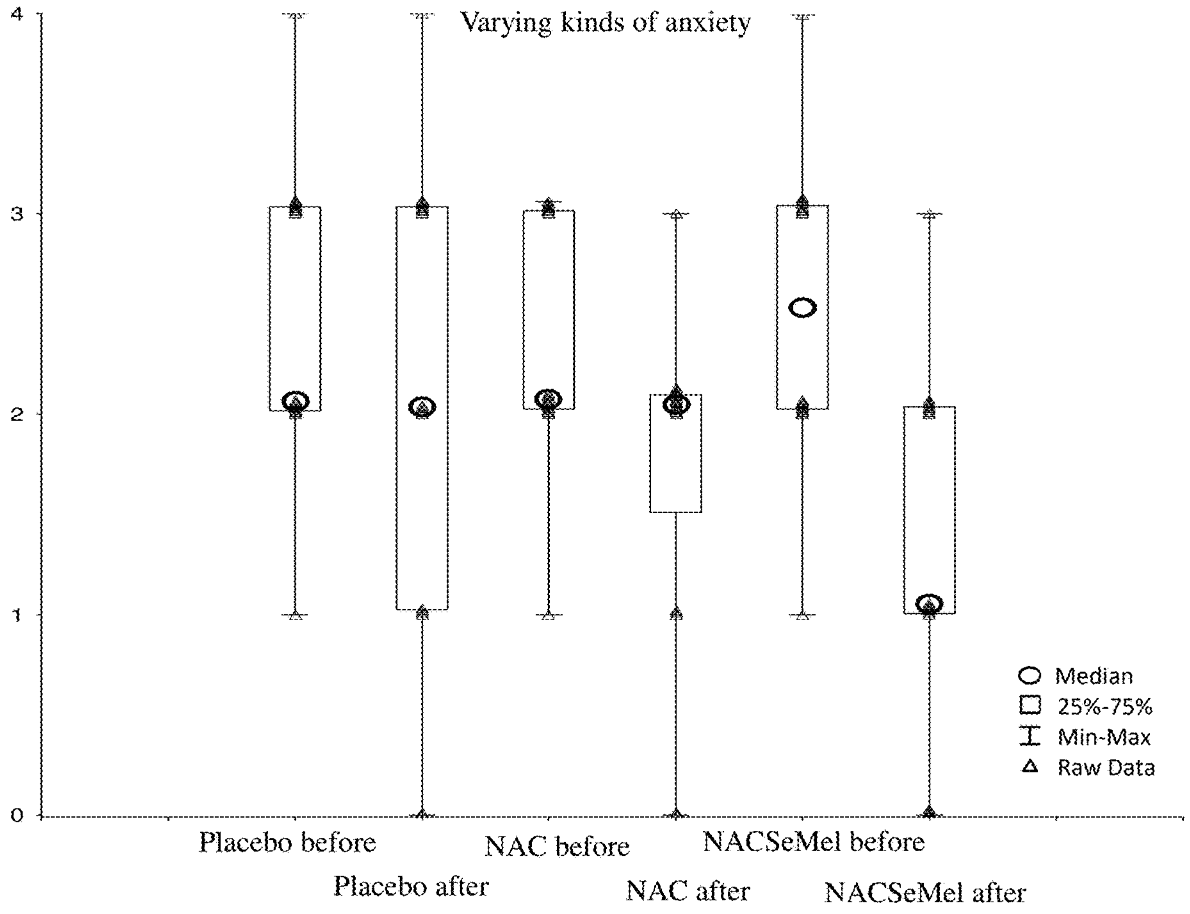
FIG. 10 illustrates the test results for treatment with Placebo, NAC and NACSeMel for a group suffering from various kinds of anxiety disorders with indications of data for intensity rating before and after treatment.

| Rated variable | Placebo | NAC | NACSeMel |
|---|---|---|---|
| Varying kinds of anxiety, n = 20, FIG. 10 | ↓7, ↑4, ~9 RP −0.10 (95% CI −0.37 to 0.18) | ↓9, ~2 RP −0.46 (95% CI −0.62 to −0.30) | ↓12 RP −0.75 (95% CI −0.91 to −0.59) |

FIG. 10 illustrates in a diagram the test results for treatment with Placebo, NAC and NACSeMel, respectively, for a group suffering from various kinds of anxiety with indications of data for pain intensity rating before and after treatment. In the diagram, a triangle indicates raw data values, a line min-max is drawn between the minimum and the maximum rating values, a box indicates the interval within which 25%-75% of the rating values occur and a circle indicates the Median value.

Specific Kinds of Anxiety Comparison—Placebo, NAC, NACSeMel

The corresponding treatment design as described above was used with patients rating the pain intensity for specific causes of anxiety, viz. Recurrent sporadic social anxiety, Social Phobia/Agoraphobia, Panic disorder, Generalized anxiety disorder, Obsessive compulsive disorder and Posttraumatic stress disorder. The results are presented in the following Table 3 and in FIG. 11-FIG. 16.

TABLE 3

Figure 11:
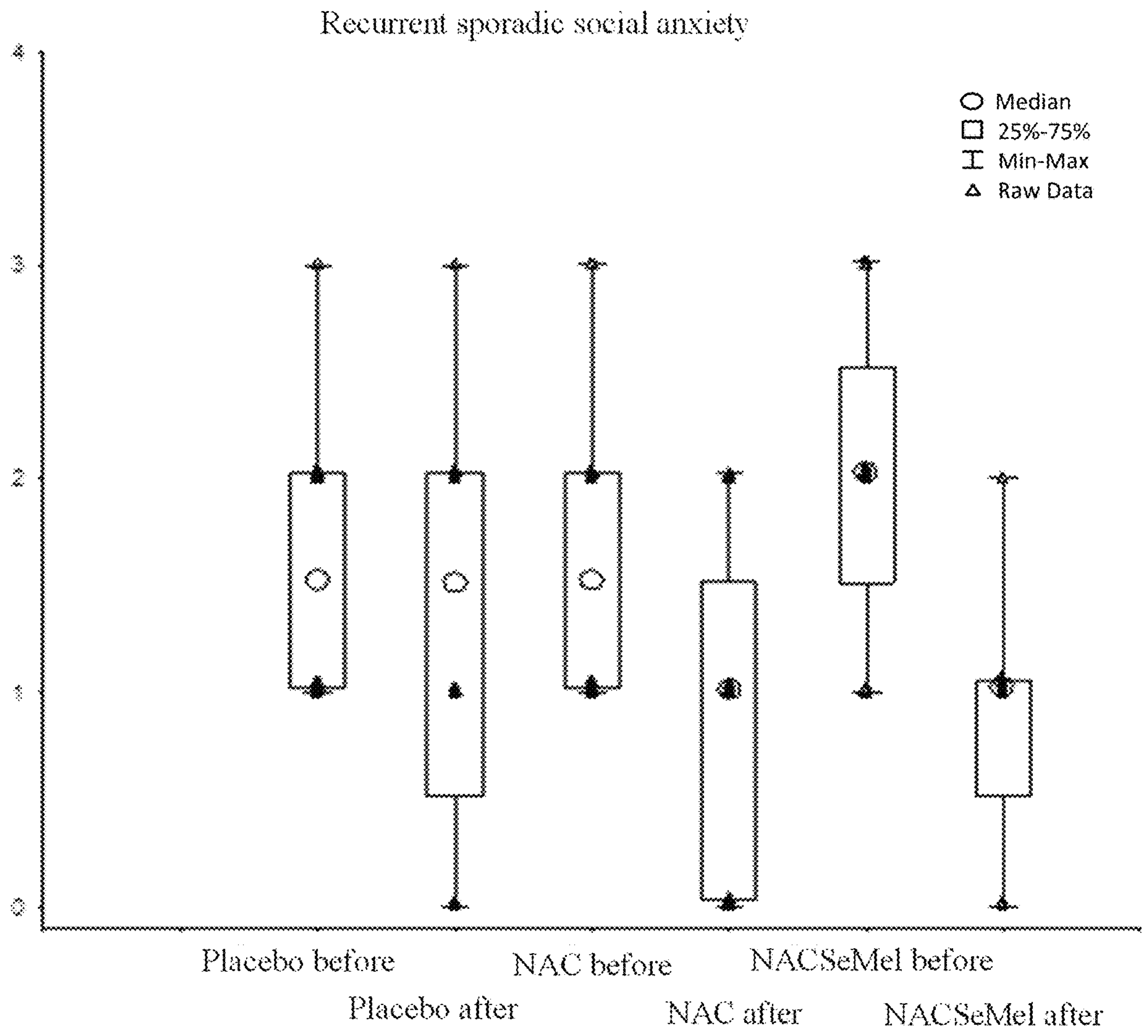
FIG. 11 illustrates the test results for treatment with Placebo, NAC and NACSeMel, for patients suffering from recurrent sporadic social anxiety.

| Rated variable | Placebo | NAC | NACSeMel |
|---|---|---|---|
| Recurrent sporadic social anxiety, n = 12, FIG. 11 | ↓5, ↑5; RP −0.13 (95% CI −0.41 to 0.16) | ↓9, ~2 RP −0.46 (95% CI −0.62 to −0.30) | ↓12 RP −0.75 (95% CI −0.91 to −0.59) |
| Social phobia, Agoraphobia, n = 6, FIG. 12 | ↓2, ~3, ↑1 RP −0.03 (95% CI −0.37 to 0.31) | ↓3, ~3 RP −0.31 (95% CI −0.55 to −0.06) | ↓6 RP −0.56 (95% CI −0.74 to −0.37) |
| Panic disorder, n = 7, FIG. 13 | ↓3, ~2, ↑2 RP −0.14 (95% CI −0.59 to 0.30) | ↓3, ~4 RP −0.35 (95% CI −0.71 to 0.01) | 5, ~2 RP −0.61 (95% CI −0.93 to −0.30) |
| Generalized anxiety disorder, n = 8, FIG. 14 | ↓2, ~4, ↑2 RP −0.13 (95% CI −0.38 to 0.32) | ↓7, ~1 RP −0.81 (95% CI −1.0 to −0.61) | RP −0.91 (95% CI −1.0 to −0.79) |
| Obsessive compulsive disorder, n = 7, FIG. 15 | ↓1, ~4, ↑2 RP 0.14 (95% CI −0.13 to 0.41) | ↓4, ~2, ↑1 RP −0.27 (95% CI −0.63 to 0.10) | ↓6, ~1 RP −0.69 (95% CI −0.96 to −0.43) |
| Posttraumatic stress disorder, n = 5, FIG. 16 | ↓1, ~3, ↑1 RP −0.04 (95% CI −0.48 to 0.40) | ↓3, ~2 RP −0.60 (95% CI −0.99 to −0.22) | ↓4, ~1 RP −0.84 (95% CI −1.0 to −0.57) |

↓ = number of patients that rated lower,
↑ = number of patients that rated higher;
~ = number of patients that rated unchanged level. The results of the test with patients rating the pain intensity due to rated recurrent sporadic social anxiety for treatment with placebo in comparison with treatment with NAC and NACSeMel are illustrated in FIG. 11.

Figure 12:
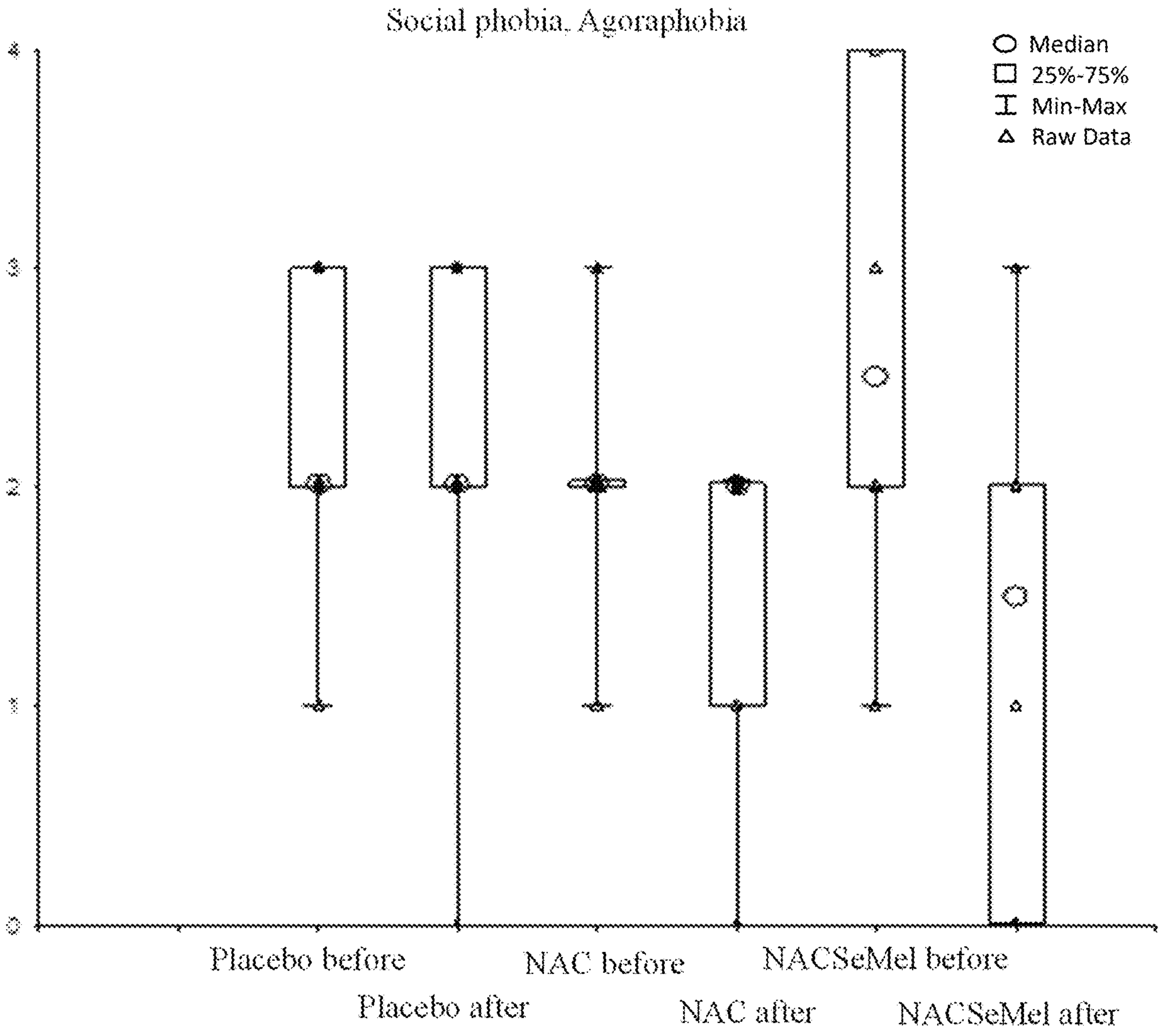
FIG. 12 illustrates the test results for treatment with Placebo, NAC and NACSeMel, for patients suffering from social phobia/agoraphobia.

The results of the test with patients rating the pain intensity due to rated social phobia/agoraphobia for treatment with placebo in comparison with treatment with NAC and NACSeMel are illustrated in FIG. 12.

Figure 13:
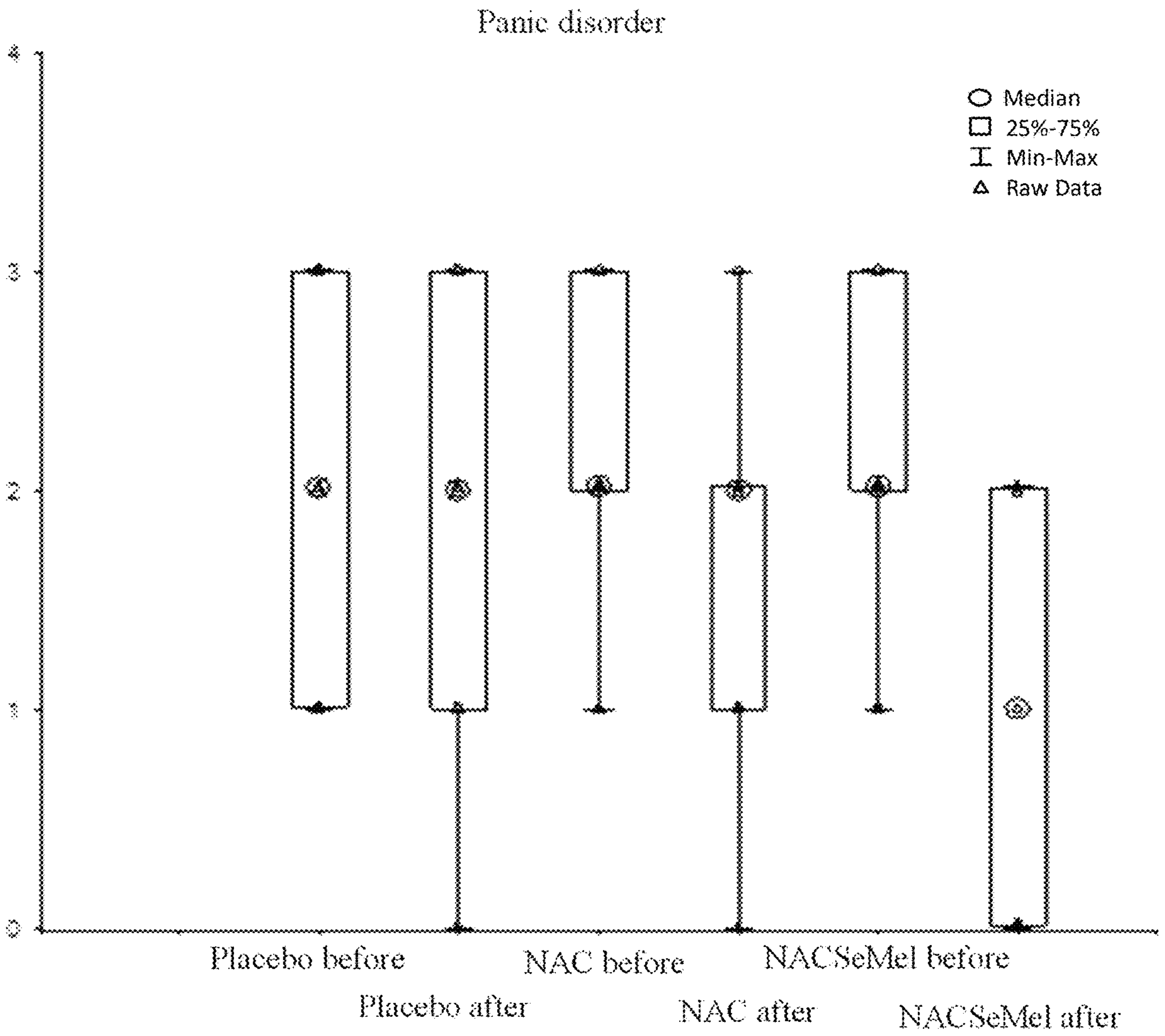
FIG. 13 illustrates the test results for treatment with Placebo, NAC and NACSeMel, for patients suffering from panic disorder.

The results of the test with patients rating the pain intensity due to rated panic disorder for treatment with placebo in comparison with treatment with NAC and NACSeMel are illustrated in FIG. 13.

Figure 14:
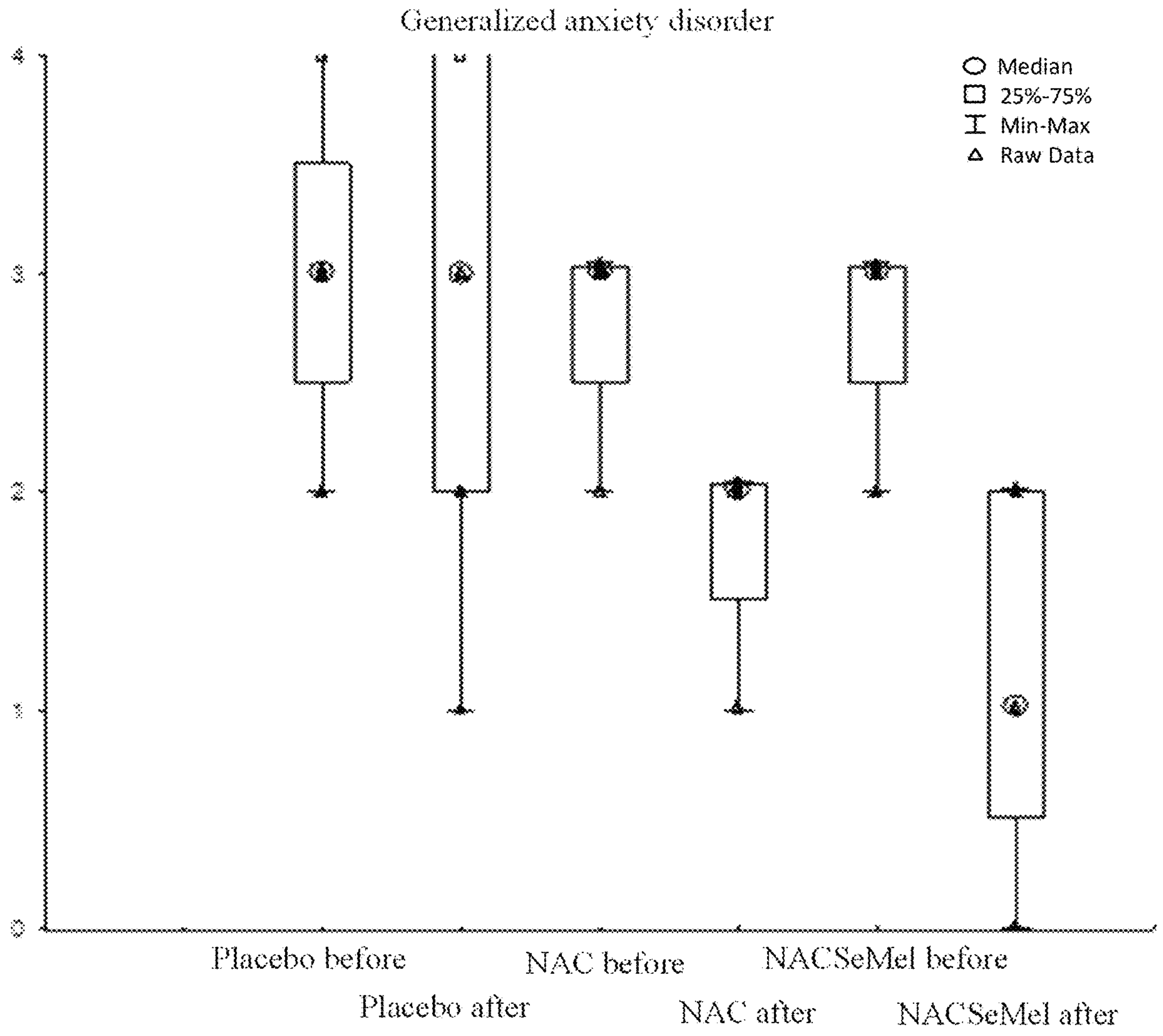
FIG. 14 illustrates the test results for treatment with Placebo, NAC and NACSeMel, for patients suffering from generalized anxiety disorder.

The results of the test with patients rating the pain intensity due to rated generalized anxiety disorder for treatment with placebo in comparison with treatment with NAC and NACSeMel are illustrated in FIG. 14.

Figure 15:
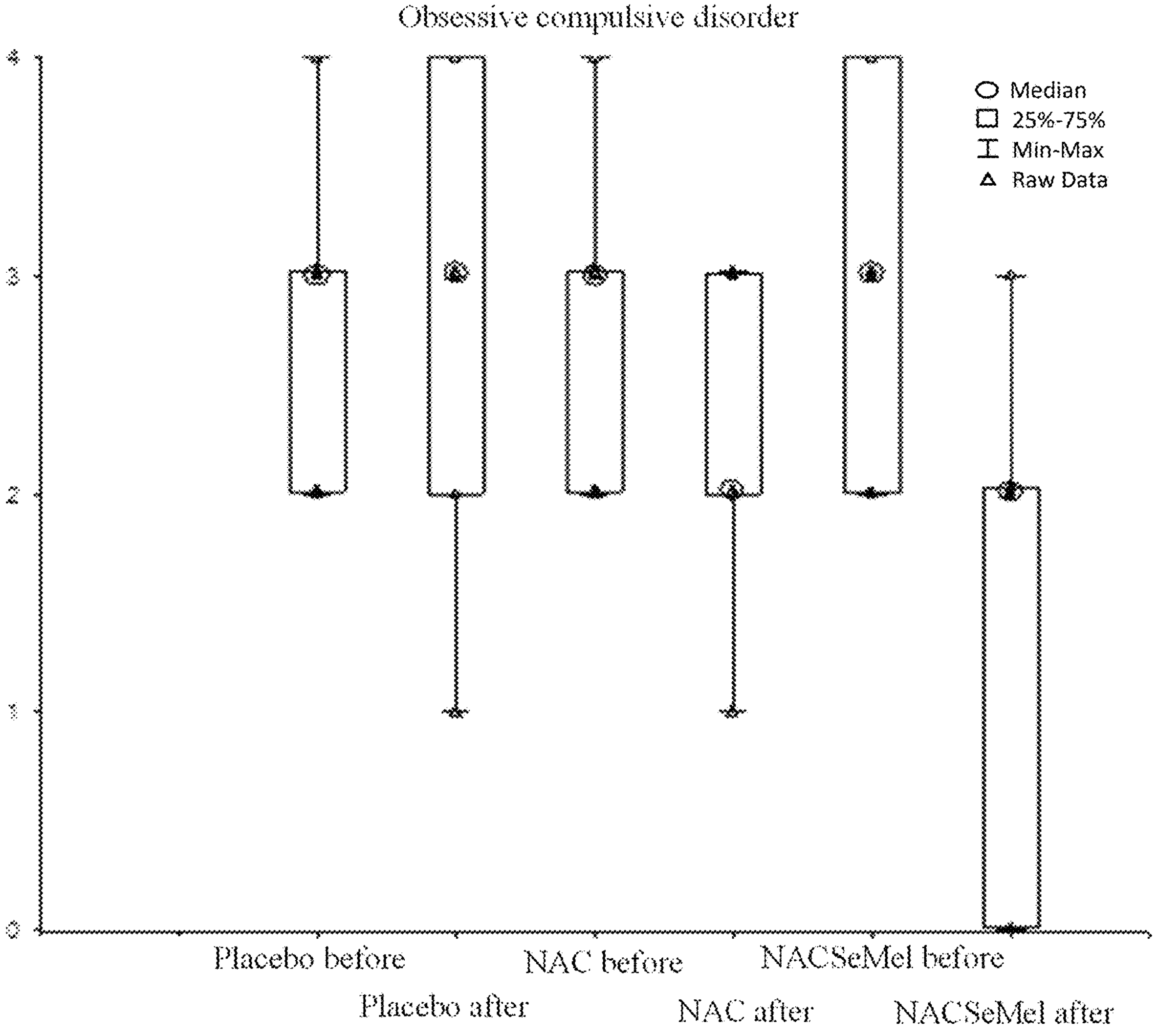
FIG. 15 illustrates the test results for treatment with Placebo, NAC and NACSeMel, for patients suffering from obsessive compulsive disorder.

The results of the test with patients rating the pain intensity due to rated obsessive compulsive disorder for treatment with placebo in comparison with treatment with NAC and NACSeMel are illustrated in FIG. 15.

Figure 16:
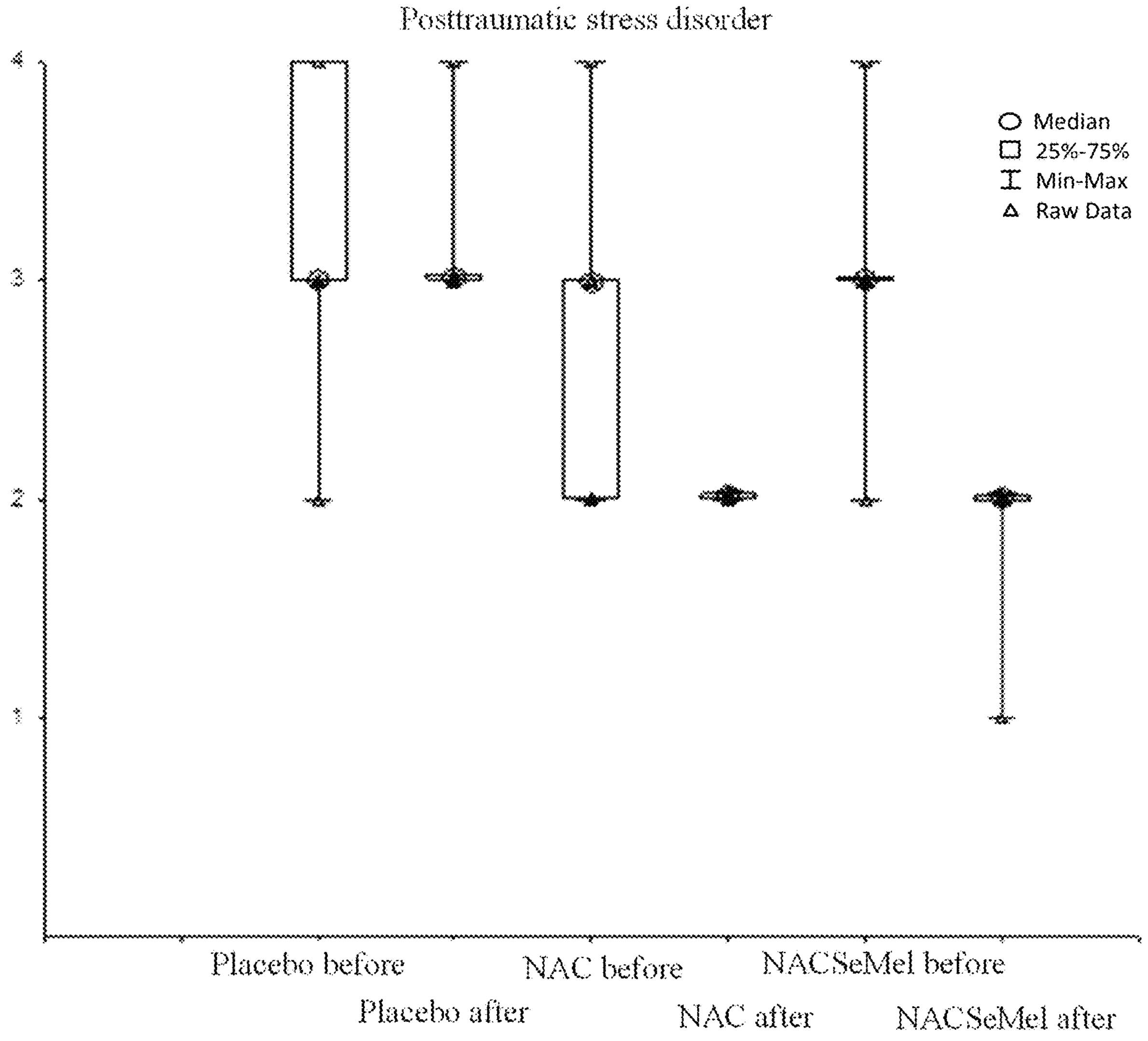
FIG. 16 illustrates the test results for treatment with Placebo, NAC and NACSeMel, for patients suffering from posttraumatic stress disorder.

The results of the test with patients rating the pain intensity due to rated posttraumatic stress disorder for treatment with placebo in comparison with treatment with NAC and NACSeMel are illustrated in FIG. 16.

In embodiments and tests as described in this section for treatment of anxiety disorder, dosages were used in accordance with the dosages described in the section Dosages further above. In embodiments, N-acetyl-L-cysteine, selenomethionine, and melatonin are administered orally or epicutaneously, or in a combination thereof. In some embodiments, at least one of N-acetyl-L-cysteine, selenomethionine, or melatonin is administered orally or epicutaneously, or both orally and epicutaneously. Other dosages and variants of administration methods are conceivable in embodiments. In one embodiment, treatment is administered epicutaneously, such as in an embodiment with 10 wt % NAC or 10 wt % NACSEMel topical gel in 5 wt % urea emulsion; for example in twice daily application for about 6 weeks. In further embodiments, N-acetyl-L-cysteine is administered at a dose in the range of about 500 mg/day to about 3000 mg/day for example in 1 to 4 doses/day, selenium in the form of selenomethionine is administered in the range of about 20 μg/day (microgram/day) to about 200 μg/day, for example about 55 μg/day and melatonin is administered in the range of about 1 to about 10 mg/day, for example about 3 mg/day.

Example 7: Effect of NAC, SeMet and Mel in the Treatment of Sporadic Insomnia In a method, conducted in a similar manner to that described in the previous Example 6, and in accordance with embodiments of this disclosure a medical product comprising NAC, SeMet and Mel in accordance with embodiments was given to a plurality of groups of patients in the treatment of sporadic insomnia. Sporadic insomnia is defined as a sleep disorder in which people have difficulties to sleep and that occurs occasionally, infrequently and/or irregularly, often arising or occurring randomly related to anxiety or with no known specific cause. A type of sporadic insomnia is caused by neurodegenerative diseases, such as sporadic fatal insomnia occurring in connection with prion protein abnormalities. The method of treating sporadic insomnia comprises administering to a patient in need thereof, a medical product consisting of one or more excipients and active agents consisting of (i) N-acetyl-L-cysteine; (ii) selenium in the form of selenomethionine; and (iii) melatonin and/or physiologically acceptable salts thereof.

Insomnia may be related and due to anxiety or have other independent causes.

In a trial, the NAC, SeMet and Mel medical product, herein also called NAC-factor 3, was administered to a group of patients in a set-up to compare the effect of placebo, NAC and the medical product consisting of NAC, SeMet and Mel in treatment of sporadic insomnia.

The patients rated their experienced intensity of insomnia before and after being exposed to medication with one of placebo, NAC and the medical product consisting of NAC, SeMet and Mel (in short NACSeMel), respectively. The subjective intensity was rated by the patients using a 5 graded verbal rating scale ranging from None/Ignorable=0, Slight=1, Moderate=2, Great=3, Excruciating=4, where the corresponding numbers 0-4 are used to illustrate the responses in accompanying graphs.

In studying the results of the rating, the change in rating that the group delivered was expressed as a measure of the group's relative position RP in order to assess whether there was a systematic change in position on the rating scale. The relative position, i.e. the change in rating is negative if the rating indicates less intensity after exposure to treatment compared to before treatment, and positive if the rating indicates higher intensity after exposure to treatment. A range of values for the relative position RP was calculated for a 95% confidence interval CI.

Results

Placebo Comparison—Placebo, NAC, NACSeMel in Treatment of Sporadic Insomnia

When a group composed of 24 patients suffering from sporadic insomnia were exposed to the placebo treatment, 9 of the 24 patients (38%) rated their intensity lower, 5 of them (20%) rated higher and 10 (42%) of them rated the same pain-intensity after as compared to before placebo treatment. The change in the group may be expressed as the measure of the group's relative position, RP, as −0.07 (95% CI −0.24 to 0.10) and confirmed that there was no systematic change in position on the rating scale for intensity after treatment with Placebo compared to before treatment.

In the same group of patients, the change in rated intensity after treatment with NAC showed that 15 patients (62%) rated lower sporadic insomnia and 9 patients (38%) rated unchanged intensity after treatment. The corresponding RP value for the group was −0.37 (95% CI −0.49 to −0.25) demonstrating a systematic change to lower intensity rating after treatment with NAC compared to before treatment.

The patients in the same group were also treated with NAC-factor 3/NACSeMel. Among the individuals all 24 patients (100%) responded with lower intensity ratings, i.e. lower sporadic insomnia after treatment than before treatment. For the change in position of the rating scale group the RP value was RP −0.62 (95% CI −0.74 to −0.49) and thereby stated a systematic change to lower levels of intensity on the rating scale, i.e. lower rating of sporadic insomnia, after treatment with NACSeMel compared to before treatment.

Figure 17:
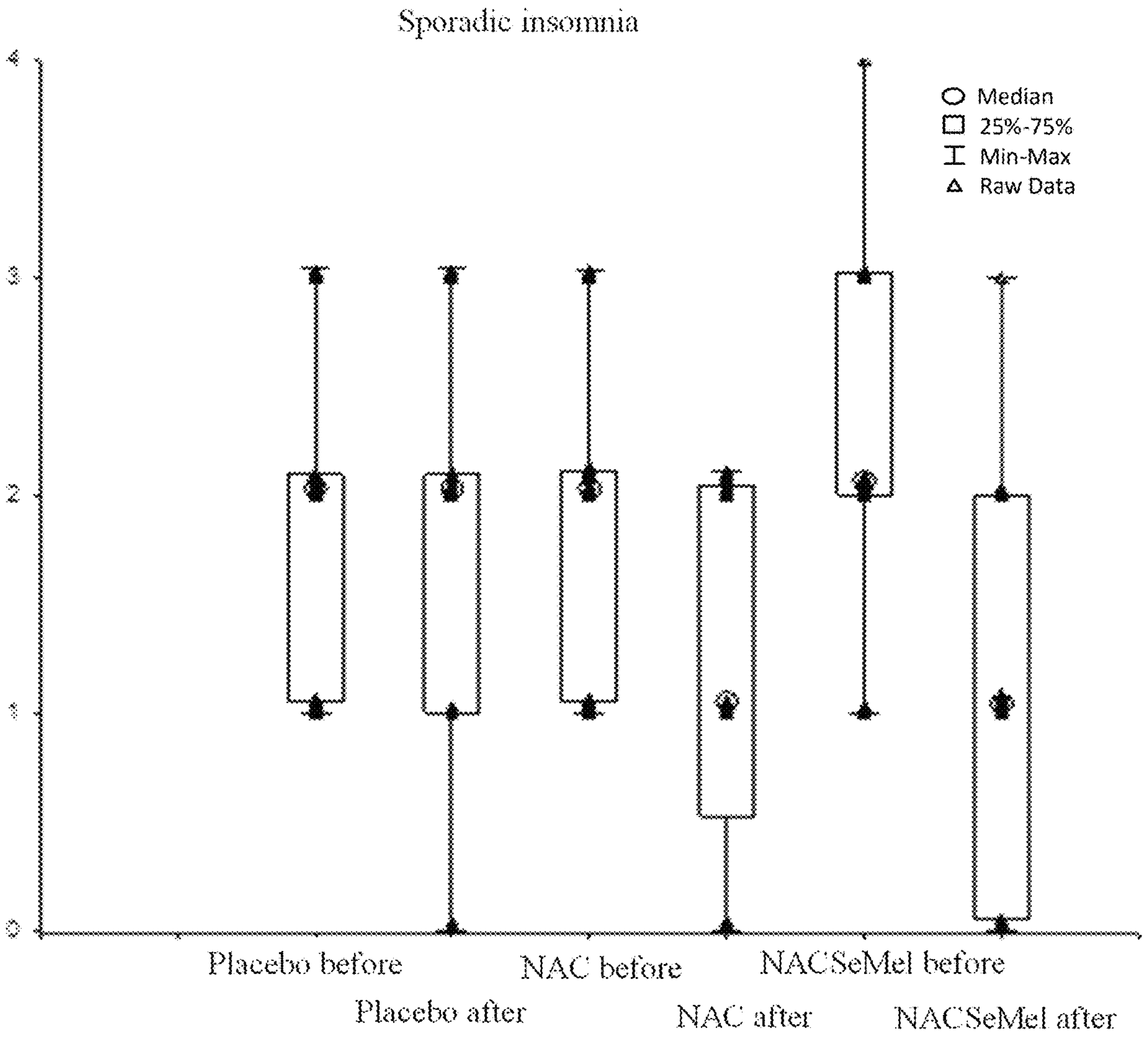
FIG. 17 illustrates the test results for treatment with Placebo, NAC and NACSeMel, for patients suffering from sporadic insomnia.

The results of the test with patients rating the intensity of sporadic insomnia for treatment with placebo in comparison with treatment with NAC and NACSeMel are illustrated in FIG. 17.

In embodiments and tests as described in this section for treatment of sporadic insomnia, dosages were used in accordance with the dosages described in the section Dosages further above. In embodiments, N-acetyl-L-cysteine, selenomethionine, and melatonin are administered orally or epicutaneously, or in a combination thereof. In some embodiments, at least one of N-acetyl-L-cysteine, selenomethionine, or melatonin is administered orally or epicutaneously, or both orally and epicutaneously. Other dosages and variants of administration methods are conceivable in embodiments. In one embodiment, treatment is administered epicutaneously, such as in an embodiment with 10 wt % NAC or 10 wt % NACSEMel topical gel in 5% urea emulsion; for example in twice daily application for about 6 weeks. In further embodiments, N-acetyl-L-cysteine is administered at a dose in the range of about 500 mg/day to about 3000 mg/day for example in 1 to 4 doses/day, selenium in the form of selenomethionine is administered in the range of about 20 μg/day (microgram/day) to about 200 μg/day, for example about 55 μg/day and melatonin is administered in the range of about 1 to about 10 mg/day, for example about 3 mg/day.

Example 8: Effect of NAC, SeMet and Mel in the Treatment of Fatigue

In a method, conducted in a similar manner to that described in the previous Examples 6 and 7, and in accordance with embodiments of this disclosure a medical product comprising NAC, SeMet and Mel in accordance with embodiments was given to a plurality of groups of patients in the treatment of fatigue. The method of treating fatigue comprises administering to a patient in need thereof, a medical product consisting of one or more excipients and active agents consisting of (i) N-acetyl-L-cysteine; (ii) selenium in the form of selenomethionine; and (iii) melatonin and/or physiologically acceptable salts thereof. Fatigue may be related and due to anxiety, and/or to sporadic insomnia or have other independent causes. Fatigue is defined as a state of tiredness that remain despite rest or sleep, and that tend to impair cognitive and/or physical ability and performance.

In a trial the NAC, SeMet and Mel medical product, herein also called NAC-factor 3, was administered to a group of patients in a set-up to compare the effect of placebo, NAC and the medical product consisting of NAC, SeMet and Mel in treatment of fatigue.

The patients rated their experienced intensity of fatigue before and after being exposed to medication with one of placebo, NAC and the medical product consisting of NAC, SeMet and Mel (in short NACSeMel), respectively. The subjective intensity was rated by the patients using a 5 graded verbal rating scale ranging from None/Ignorable=0, Slight=1, Moderate=2, Great=3, Excruciating=4, where the corresponding numbers 0-4 are used to illustrate the responses in accompanying graphs.

In studying the results of the rating, the change in rating that the group delivered was expressed as a measure of the group's relative position RP in order to assess whether there was a systematic change in position on the rating scale. The relative position, i.e. the change in rating is negative if the rating indicates less intensity after exposure to treatment compared to before treatment, and positive if the rating indicates higher intensity after exposure to treatment. A range of values for the relative position RP was calculated for a 95% confidence interval CI.

Results

Placebo Comparison—Placebo, NAC, NACSeMel in Treatment of Fatigue

When a group composed of 20 patients suffering from fatigue were exposed to the placebo treatment, 4 of the 24 patients (20%) rated their intensity of fatigue lower, 8 of them (40%) rated higher and 8 (40%) of them rated the same intensity of fatigue after as compared to before placebo treatment. The change in the group may be expressed as the measure of the group's relative position, RP, as 0.16 (95% CI −0.04 to 0.35) and confirmed that there was no systematic change in position on the rating scale for intensity of fatigue after treatment with Placebo compared to before treatment.

In the same group of 20 patients, the change in rated intensity of fatigue after treatment with NAC showed that 9 patients (45%) rated lower fatigue, 3 patients (15%) rated increased level of fatigue and 8 patients (40%) rated unchanged intensity of fatigue after treatment. The corresponding RP value for the group was −0.26 (95% CI −0.49 to −0.03) demonstrating a systematic change to lower intensity rating after treatment with NAC compared to before treatment.

The patients in the same group were also treated with NAC-factor 3/NACSeMel. Among the individuals, 18 patients (90%) responded with lower fatigue ratings, i.e. lower fatigue after treatment than before treatment, and the remaining 2 patients (10%) responded with unchanged or higher fatigue. For the change in position of the rating scale group the RP value was RP −0.68 (95% CI −0.83 to −0.53) and thereby stated a systematic change to lower levels of intensity on the rating scale, i.e. lower rating of fatigue, after treatment with NACSeMel compared to before treatment.

Figure 18:
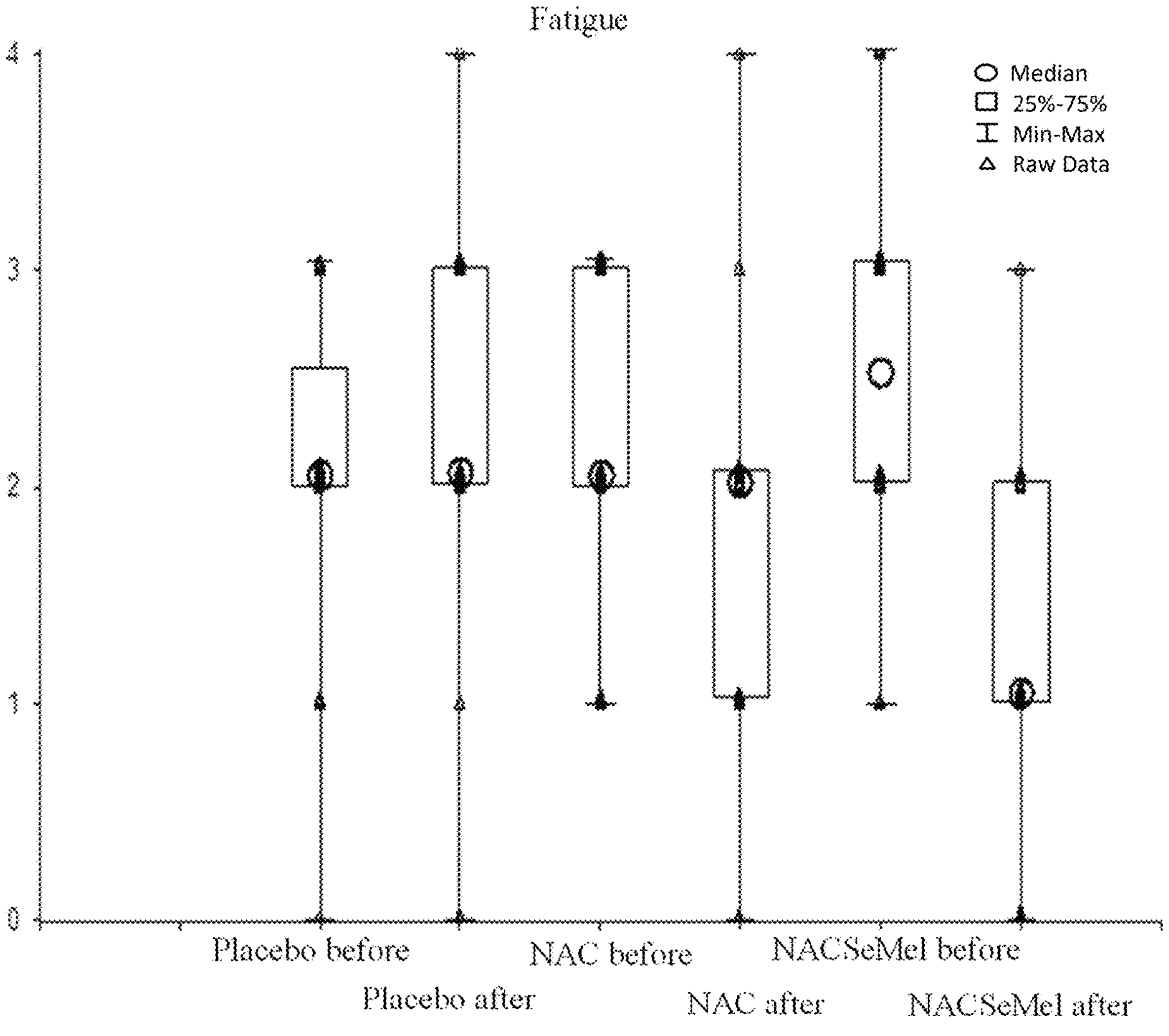
FIG. 18 illustrates the test results for treatment with Placebo, NAC and NACSeMel, for patients suffering from fatigue.

The results of the test with patients rating the intensity of fatigue for treatment with placebo in comparison with treatment with NAC and NACSeMel are illustrated in FIG. 18.

In embodiments and tests as described in this section, dosages for treatment of fatigue were used in accordance with the dosages described in the section Dosages further above. In embodiments, N-acetyl-L-cysteine, selenomethionine, and melatonin are administered orally or epicutaneously, or in a combination thereof. In some embodiments, at least one of N-acetyl-L-cysteine, selenomethionine, or melatonin is administered orally or epicutaneously, or both orally and epicutaneously. Other dosages and variants of administration methods are conceivable in embodiments. In one embodiment, treatment is administered epicutaneously, such as in an embodiment with 10 wt % NAC or 10 wt % NACSEMel topical gel in 5% urea emulsion; for example in twice daily application for about 6 weeks. In further embodiments, N-acetyl-L-cysteine is administered at a dose in the range of about 500 mg/day to about 3000 mg/day for example in 1 to 4 doses/day, selenium in the form of selenomethionine is administered in the range of about 20 μg/day (microgram/day) to about 200 μg/day, for example about 55 μg/day and melatonin is administered in the range of about 1 to about 10 mg/day, for example about 3 mg/day.

What is claimed is:

1. A method of treating an anxiety disorder, the method comprising:

administering to a patient in need thereof, a medical product consisting of one or more excipients and active agents consisting of:

(i) N-acetyl-L-cysteine;

(ii) selenium in the form of selenomethionine; and (iii) melatonin and/or physiologically acceptable salts thereof.

2. The method of claim 1, wherein the anxiety disorder is sporadic insomnia.

3. The method of claim 1, wherein the anxiety disorder is fatigue.

4. The method of claim 1, wherein the medical product consisting of one or more excipients and active agents consisting of N-acetyl-L-cysteine, selenomethionine, and melatonin and/or physiologically acceptable salts thereof is administered orally.

5. The method of claim 1, wherein components (i)-(iii) are provided as separate dosage units.

6. The method of claim 1, wherein the N-acetyl-L-cysteine is administered at a dose of 45 mg/kg/day, the selenomethionine is administered at a dose of 0.4-1.2 μg/kg/day, and the melatonin is administered at a dose of 0.02-0.08 mg/kg/day.

7. The method of claim 6, wherein the N-acetyl-L-cysteine is administered at a dose of 20-30 mg/kg/day, the selenomethionine is administered at a dose of 0.8 μg/kg/day, and the melatonin is administered at a dose of 0.04 mg/kg/day.

8. The method of claim 1, wherein the N-acetyl-L-cysteine is administered at a dose of about 500 mg/day to about 3000 mg/day, the selenomethionine is administered at a dose of about 20 μg/day to about 200 μg/day, and the melatonin is administered at a dose of about 1 to about 10 mg/day.

9. The method of claim 8, wherein the selenomethionine is administered at a dose of about 55 μg/day, and the melatonin is administered at a dose of about 3 mg/day.

10. The method of claim 1, wherein the anxiety disorder is selected from the group consisting of generalized anxiety disorder (GAD), panic disorder, social phobia, agoraphobia, obsessive-compulsive disorder (OCD), posttraumatic stress disorder, sporadic insomnia and/or fatigue.

11. The method of claim 1, wherein the anxiety disorder is generalized anxiety disorder (GAD).

12. The method of claim 1, wherein the anxiety disorder is panic disorder.

13. The method of claim 1, wherein the anxiety disorder is social phobia.

14. The method of claim 1, wherein the anxiety disorder is agoraphobia.

15. The method of claim 1, wherein the anxiety disorder is obsessive-compulsive disorder (OCD).

16. The method of claim 1, wherein the anxiety disorder is posttraumatic stress disorder.

* * * * *

SEQUENCE LISTING

```
Sequence total quantity: 12
SEQ ID NO: 1           moltype = DNA  length = 21
FEATURE                Location/Qualifiers
misc_feature           1..21
                       note = Synthetic Oligonucleotide SI Forward Primer
source                 1..21
                       mol_type = other DNA
                       organism = synthetic construct
SEQUENCE: 1
acgatgggga ggacactggc t                                          21

SEQ ID NO: 2           moltype = DNA  length = 21
FEATURE                Location/Qualifiers
misc_feature           1..21
                       note = Synthetic Oligonucleotide SI Reverse Primer
source                 1..21
                       mol_type = other DNA
                       organism = synthetic construct
SEQUENCE: 2
tccaagttgc atccagcggg t                                          21

SEQ ID NO: 3           moltype = DNA  length = 20
FEATURE                Location/Qualifiers
misc_feature           1..20
                       note = Synthetic Oligonucleotide ALPI Forward Primer
source                 1..20
                       mol_type = other DNA
                       organism = synthetic construct
```

```
SEQUENCE: 3
gtatgtgtgg aaccgcactg                                              20

SEQ ID NO: 4            moltype = DNA  length = 20
FEATURE                 Location/Qualifiers
misc_feature            1..20
                        note = Synthetic Oligonucleotide ALPI Reverse Primer
source                  1..20
                        mol_type = other DNA
                        organism = synthetic construct
SEQUENCE: 4
ctggtaagcc acaccctcat                                              20

SEQ ID NO: 5            moltype = DNA  length = 20
FEATURE                 Location/Qualifiers
misc_feature            1..20
                        note = Synthetic Oligonucleotide CLDN1 Forward Primer
source                  1..20
                        mol_type = other DNA
                        organism = synthetic construct
SEQUENCE: 5
tggctgtcat tgggggtgcg                                              20

SEQ ID NO: 6            moltype = DNA  length = 20
FEATURE                 Location/Qualifiers
misc_feature            1..20
                        note = Synthetic Oligonucleotide CLDN1 Reverse Primer
source                  1..20
                        mol_type = other DNA
                        organism = synthetic construct
SEQUENCE: 6
gcagcagccc agccagtgaa                                              20

SEQ ID NO: 7            moltype = DNA  length = 20
FEATURE                 Location/Qualifiers
misc_feature            1..20
                        note = Synthetic Oligonucleotide PCDH1 Forward Primer
source                  1..20
                        mol_type = other DNA
                        organism = synthetic construct
SEQUENCE: 7
cctatccagc ctgagctttg                                              20

SEQ ID NO: 8            moltype = DNA  length = 20
FEATURE                 Location/Qualifiers
misc_feature            1..20
                        note = Synthetic Oligonucleotide PCDH1 Reverse Primer
source                  1..20
                        mol_type = other DNA
                        organism = synthetic construct
SEQUENCE: 8
ggcagtgata tagggtgcgt                                              20

SEQ ID NO: 9            moltype = DNA  length = 20
FEATURE                 Location/Qualifiers
misc_feature            1..20
                        note = Synthetic Oligonucleotide P21/cdkn1a Forward Primer
source                  1..20
                        mol_type = other DNA
                        organism = synthetic construct
SEQUENCE: 9
tgagctgcgc cagctgaggt                                              20

SEQ ID NO: 10           moltype = DNA  length = 20
FEATURE                 Location/Qualifiers
misc_feature            1..20
                        note = Synthetic Oligonucleotide P21/cdkn1a Reverse Primer
source                  1..20
                        mol_type = other DNA
                        organism = synthetic construct
SEQUENCE: 10
gctgctcgct gtccactggg                                              20

SEQ ID NO: 11           moltype = DNA  length = 19
FEATURE                 Location/Qualifiers
misc_feature            1..19
                        note = Synthetic Oligonucleotide GADPH Forward Primer
source                  1..19
                        mol_type = other DNA
```

-continued

```
                        organism = synthetic construct
SEQUENCE: 11
gtcagtggtg gacctgacc                                                19

SEQ ID NO: 12           moltype = DNA  length = 20
FEATURE                 Location/Qualifiers
misc_feature            1..20
                        note = Synthetic Oligonucleotide GADPH Reverse Primer
source                  1..20
                        mol_type = other DNA
                        organism = synthetic construct
SEQUENCE: 12
aggggtctac atggcaactg                                               20
```